(12) United States Patent
Yoshioka et al.

(10) Patent No.: US 8,667,302 B2
(45) Date of Patent: Mar. 4, 2014

(54) SIGNATURE GENERATING DEVICE AND METHOD, SIGNATURE VERIFYING DEVICE AND METHOD, AND COMPUTER PRODUCT

(75) Inventors: Takashi Yoshioka, Kawasaki (JP); Masahiko Takenaka, Kawasaki (JP); Fumitsugu Matsuo, Shinjuku (JP); Fumiaki Chiba, Kawasaki (JP)

(73) Assignees: Fujitsu Limited, Kawasaki (JP); Fujitsu Advanced Engineering Limited, Shinjuku (JP)

( * ) Notice: Subject to any disclaimer, the term of this patent is extended or adjusted under 35 U.S.C. 154(b) by 338 days.

(21) Appl. No.: 12/888,553

(22) Filed: Sep. 23, 2010

(65) Prior Publication Data

US 2011/0078459 A1    Mar. 31, 2011

(30) Foreign Application Priority Data

Sep. 30, 2009    (JP) ................................. 2009-227783

(51) Int. Cl.
*G06F 21/24* (2006.01)

(52) U.S. Cl.
USPC .......................................................... 713/189

(58) Field of Classification Search
None
See application file for complete search history.

(56) References Cited

U.S. PATENT DOCUMENTS

| | | | | |
|---|---|---|---|---|
| 5,960,081 | A * | 9/1999 | Vynne et al. | 713/176 |
| 7,996,679 | B2 * | 8/2011 | Hsu et al. | 713/176 |
| 8,091,015 | B2 * | 1/2012 | Yoshioka et al. | 715/201 |
| 8,103,050 | B2 * | 1/2012 | Lefebvre et al. | 382/100 |
| 8,204,314 | B2 * | 6/2012 | Lu et al. | 382/218 |
| 2005/0053239 | A1 | 3/2005 | Nomizu | |
| 2005/0204248 | A1 | 9/2005 | Matsui | |
| 2007/0050713 | A1 * | 3/2007 | Yoshioka et al. | 715/530 |
| 2007/0079126 | A1 * | 4/2007 | Hsu et al. | 713/176 |
| 2008/0100854 | A1 | 5/2008 | Komatsu | |
| 2008/0256362 | A1 | 10/2008 | Takenaka et al. | |
| 2009/0164793 | A1 | 6/2009 | Yoshioka et al. | |
| 2010/0312908 | A1 | 12/2010 | Yoshioka | |
| 2011/0150269 | A1 * | 6/2011 | Yoshioka | 382/100 |

FOREIGN PATENT DOCUMENTS

| | | | | |
|---|---|---|---|---|
| EP | 1498799 | A2 * | 1/2005 | ................ G06F 1/00 |
| JP | 2002-259216 | | 9/2002 | |
| JP | 2003-022007 | | 1/2003 | |

(Continued)

OTHER PUBLICATIONS

Office Action of Japan Patent Application 2009-227783 dated Oct. 22, 2013.

(Continued)

*Primary Examiner* — Fikremariam A Yalew
(74) *Attorney, Agent, or Firm* — Staas & Halsey LLP

(57) ABSTRACT

A signature generating device includes a receiving unit that receives a sequence of data; a summary data generating unit that generates summary data of the data upon reception of each of the data by the receiving unit; an obtaining unit that obtains, when the number of data included in a sequence of the generated summary data reaches a given number, the sequence of the summary data as a block; a setting unit that sets, as a signature subject, a current block constituted by the sequence of the summary data, and the summary data selected from at least one block contiguous to the current block; a digital signature generating unit that generates a digital signature concerning data summarized for the current block; and a sending unit that sends the generated digital signature, the signature subject associated with the digital signature, and the data summarized for the current block.

18 Claims, 24 Drawing Sheets

(56) References Cited

FOREIGN PATENT DOCUMENTS

| JP | 2004-165778 | 6/2004 |
|---|---|---|
| JP | 2008-060745 | 3/2008 |
| JP | 2008-110575 | 5/2008 |
| JP | 2008-178048 | 7/2008 |
| JP | 2009-128956 | 6/2009 |
| JP | 2009-152713 | 7/2009 |
| JP | 2009-253305 | 10/2009 |
| JP | 2010-107832 | 5/2010 |
| WO | 2004-068350 | 8/2004 |
| WO | 2006/008847 | 1/2006 |
| WO | 2009-104284 | 8/2009 |

OTHER PUBLICATIONS

Extended European Search Report mailed Nov. 8, 2013 in corresponding European Application No. 10181083.6.
Rosario Gennaro et al., "How to Sign Digital Streams", Advances in Cryptology—Crypto '97, Proceedings of the Annual International Cryptology Conference, Aug. 17, 1997, pp. 180-197.

* cited by examiner

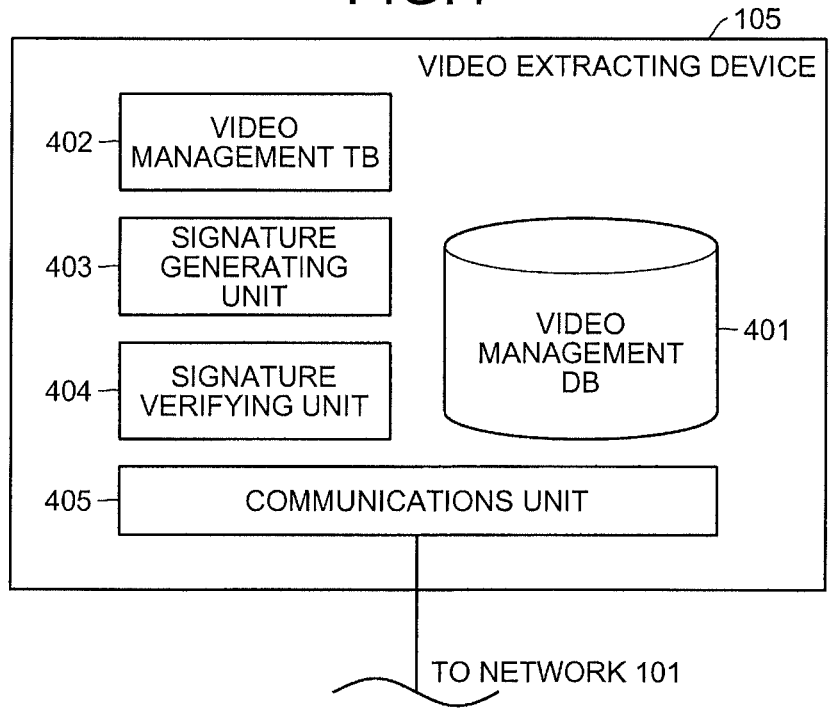
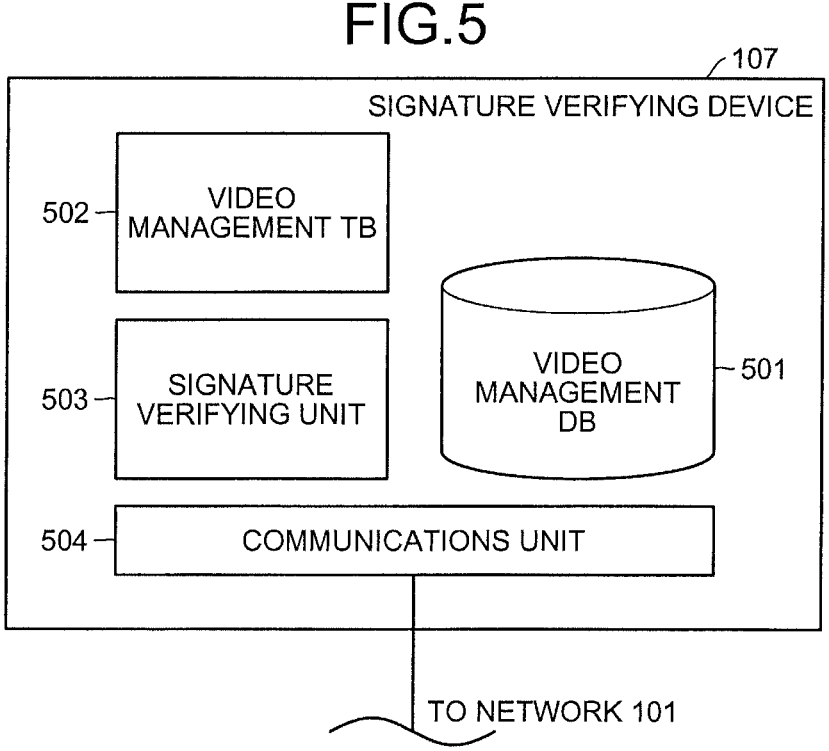

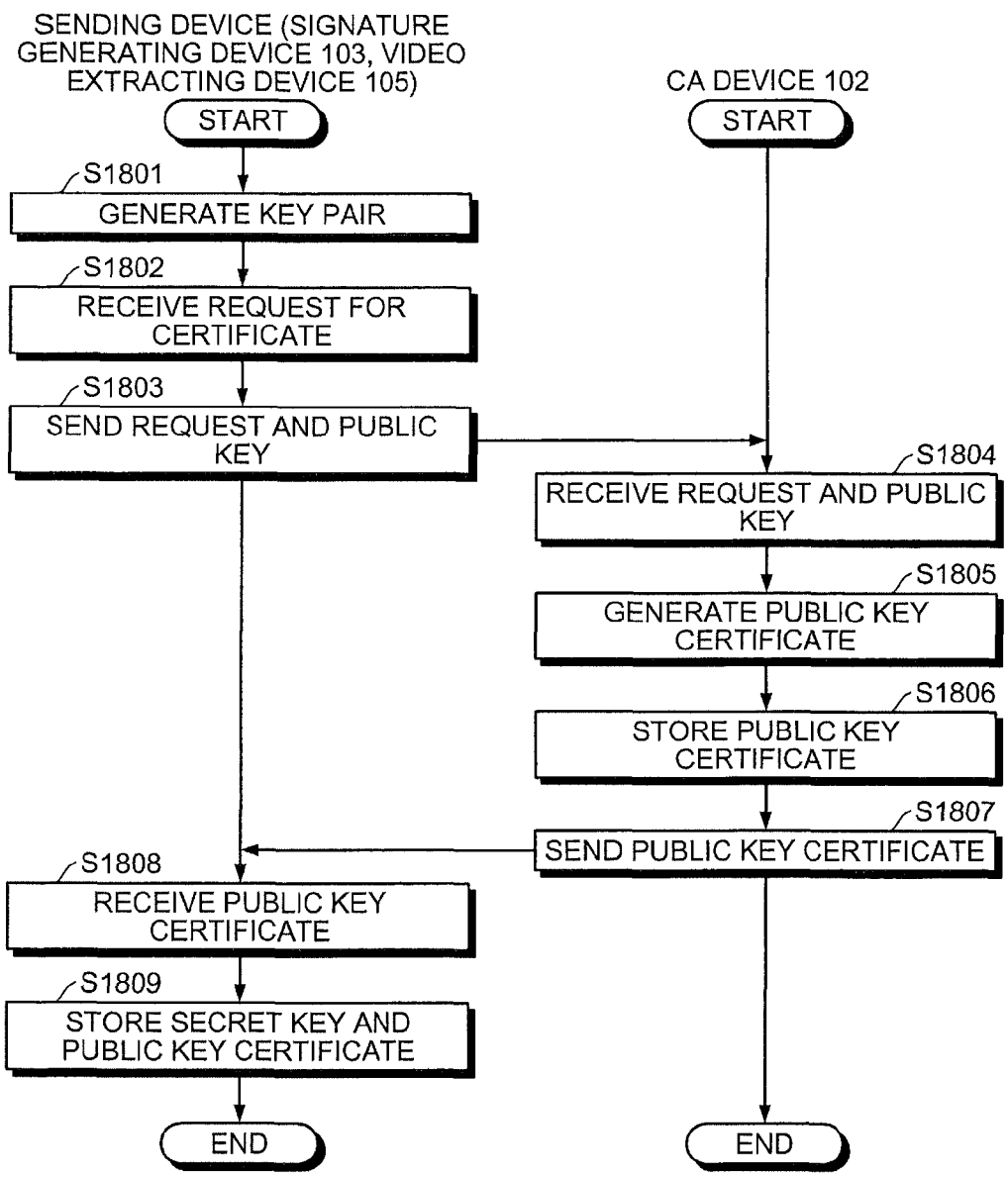

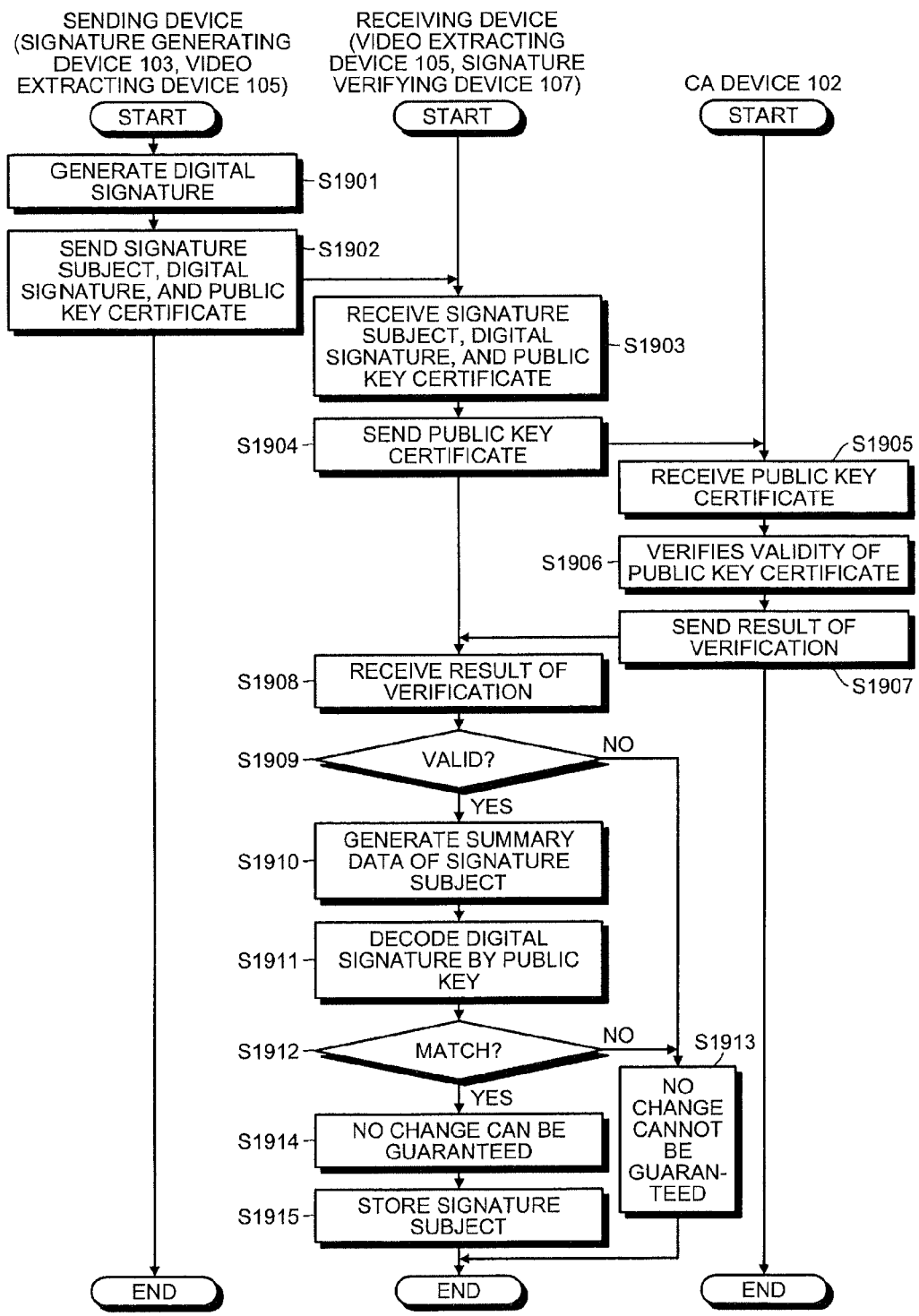

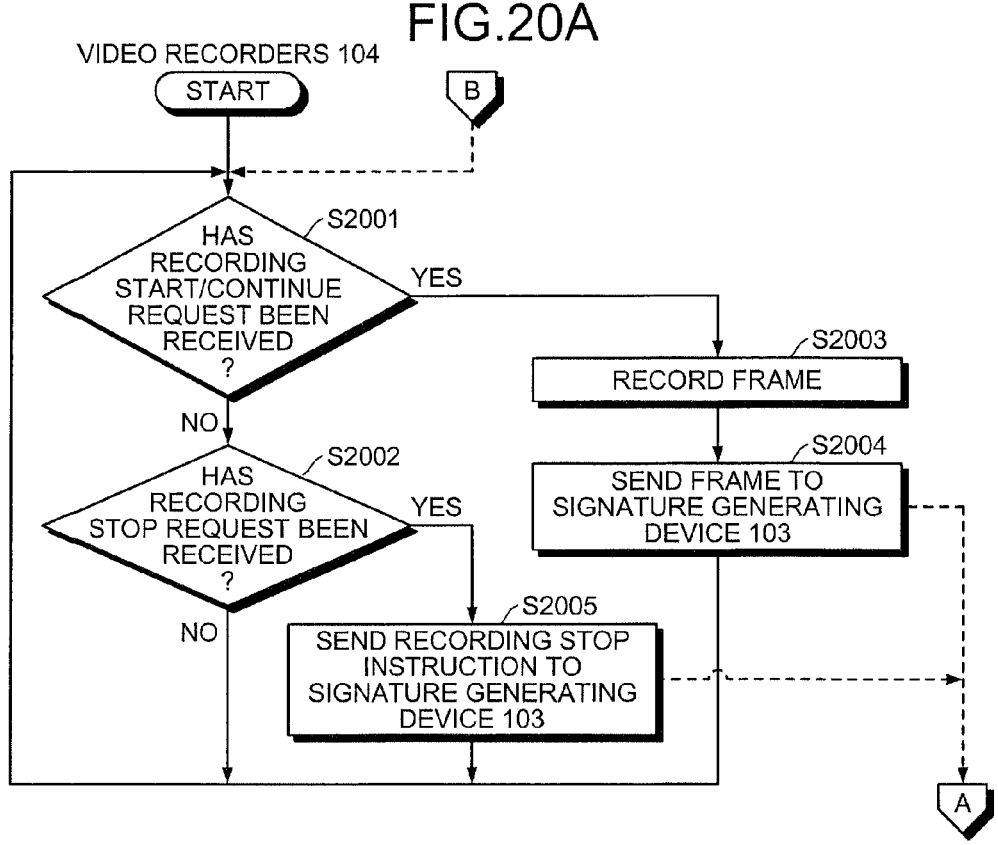

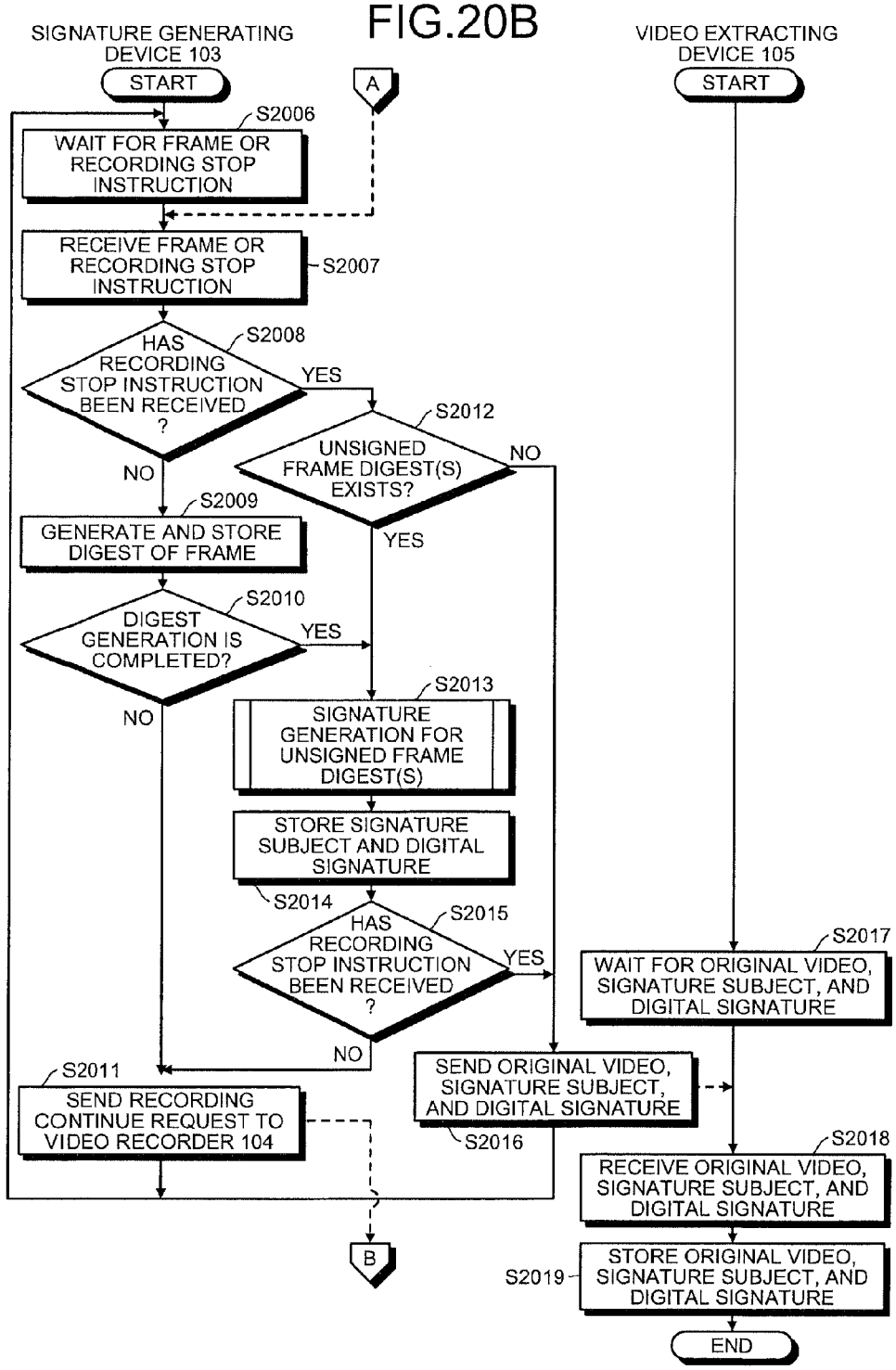

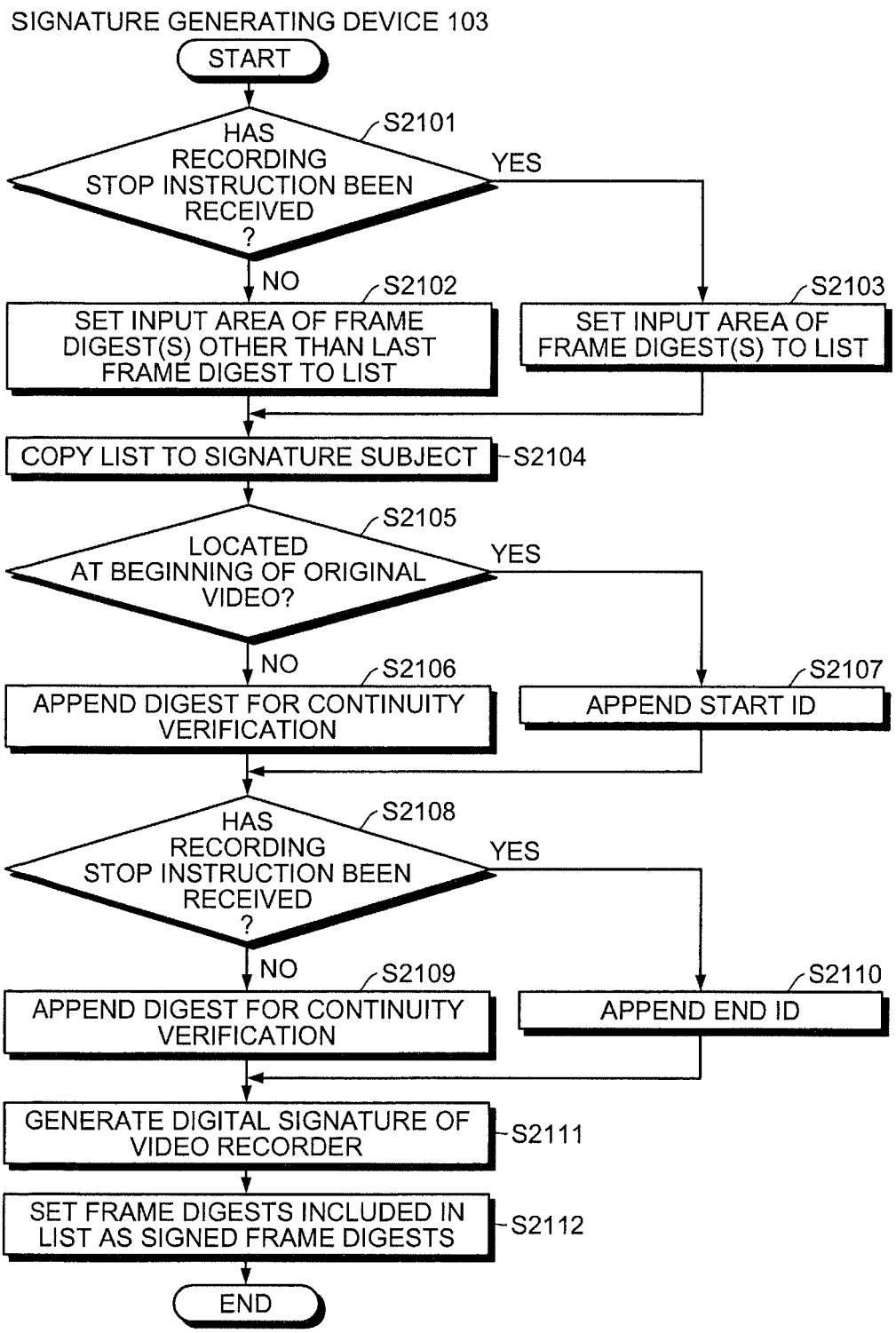

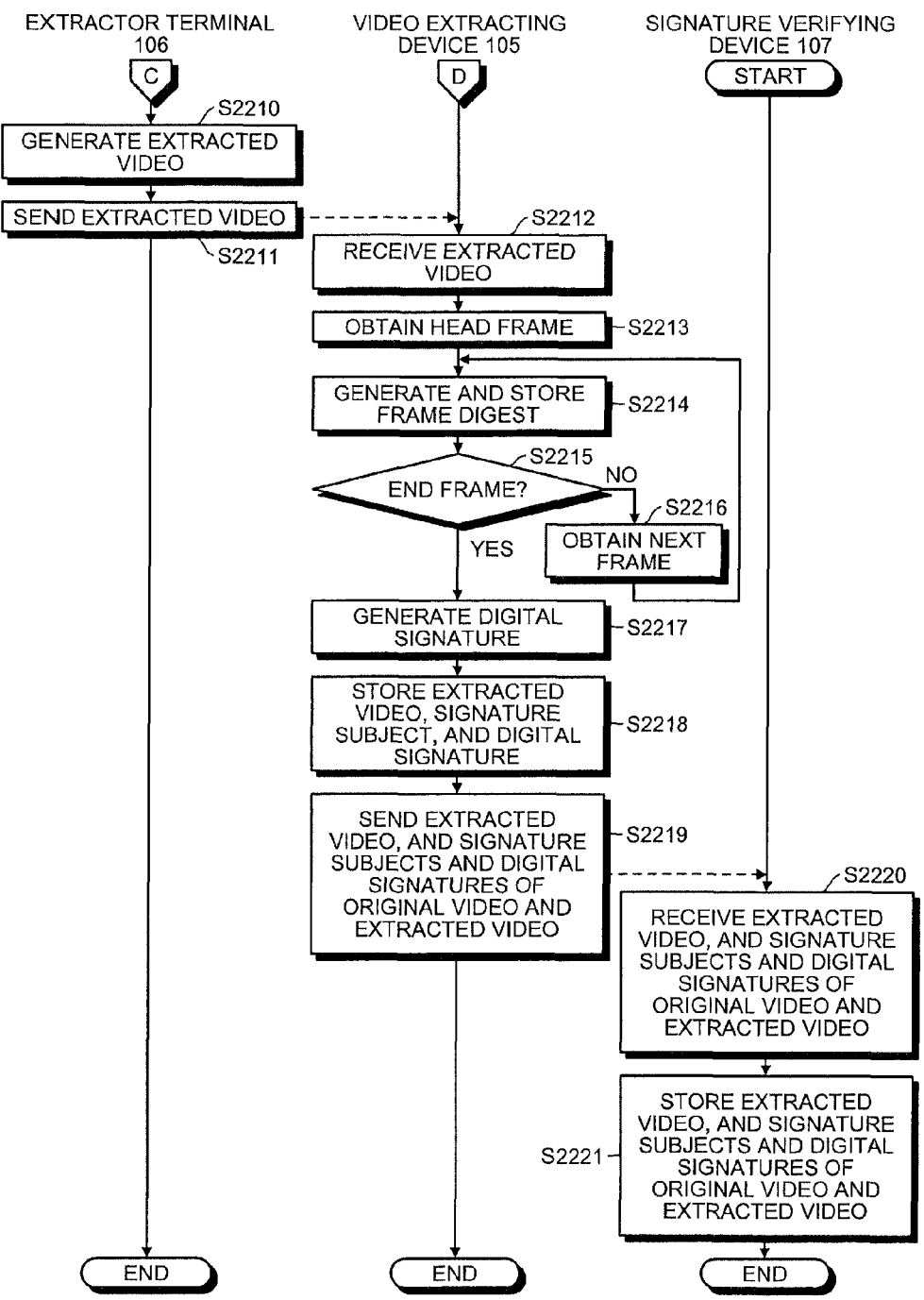

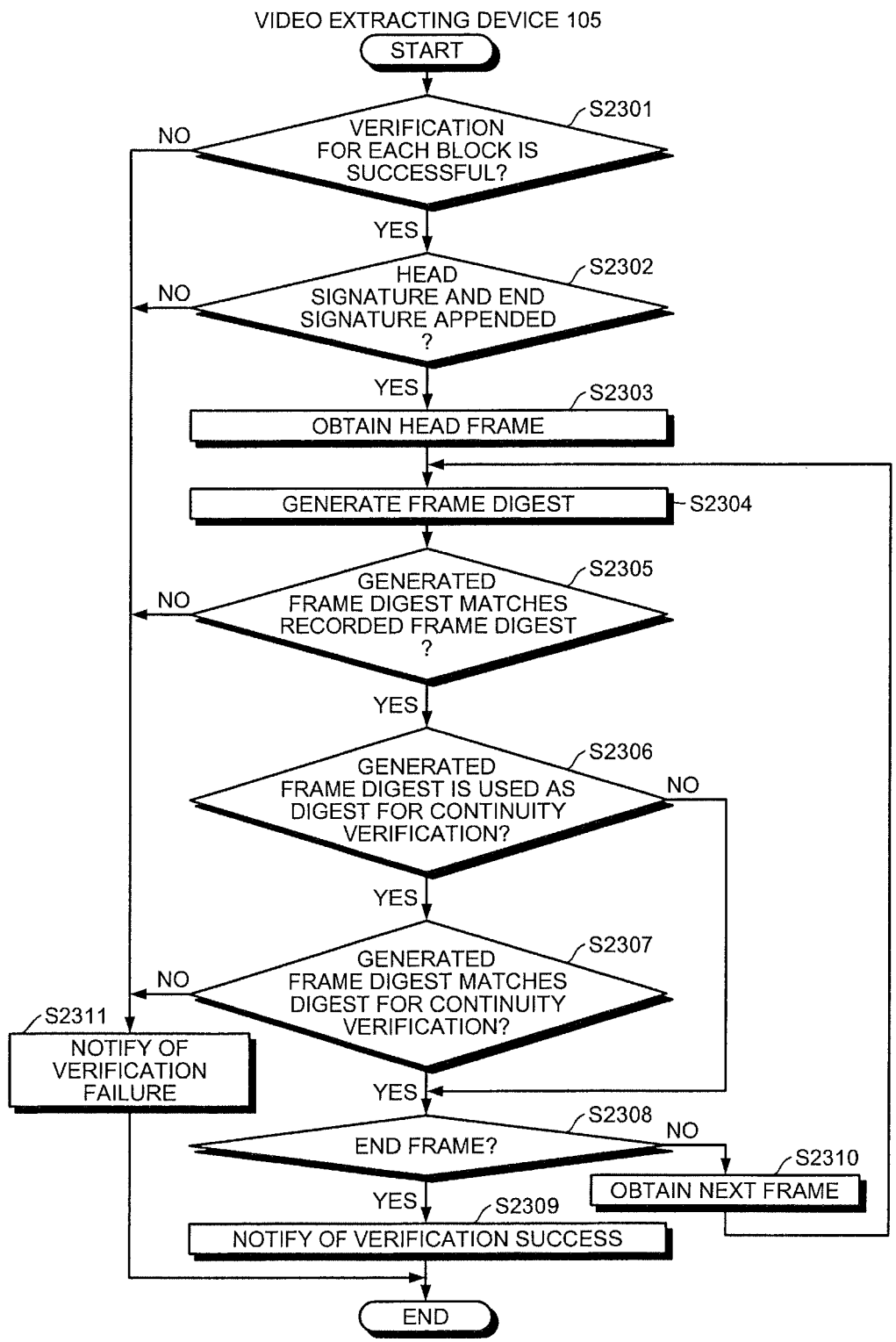

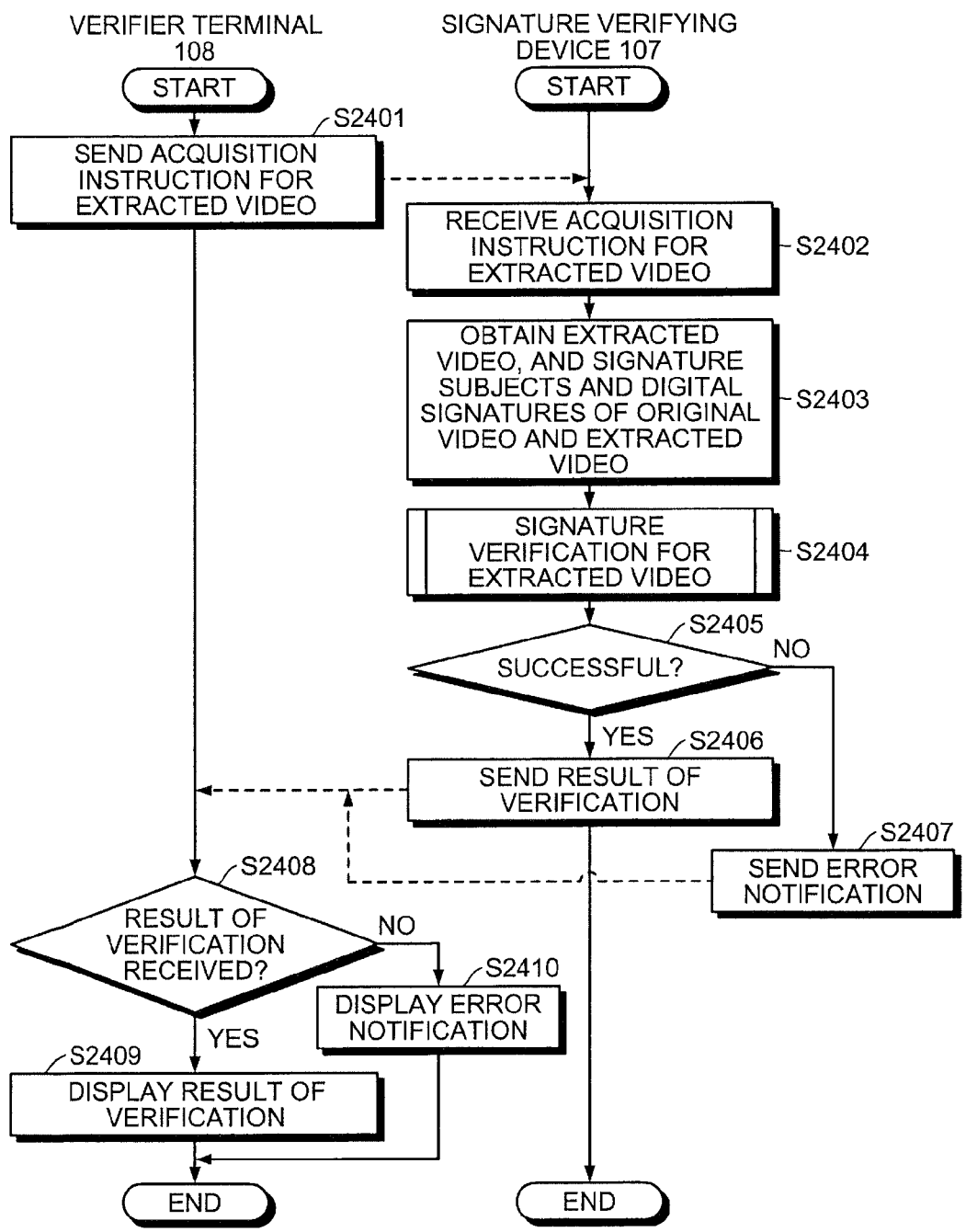

SIGNATURE GENERATING DEVICE AND METHOD, SIGNATURE VERIFYING DEVICE AND METHOD, AND COMPUTER PRODUCT

CROSS REFERENCE TO RELATED APPLICATIONS

This application is based upon and claims the benefit of priority of the prior Japanese Patent Application No. 2009-227783, filed on Sep. 30, 2009, the entire contents of which are incorporated herein by reference.

FIELD

The embodiments discussed herein are related to signature generation and verification.

BACKGROUND

The installation of surveillance cameras in stores, downtowns, and apartments and the installation of drive recorders in business vehicles have recently become common, and video is increasingly treated as evidence. As a countermeasure for trouble occurring with transactions and support services through telecommunications, it has also become common for vendors to record conversations between customers and operators as evidence.

Currently, when video and audio are used as evidence, videotapes and/or video/audio files are submitted as they are. However, video and audio can be easily falsified and/or edited along with the digitization thereof, and thus, third-party certification such as a signature and a timestamp is required when audio and video are treated as evidence. Products and services for recording telephone operator conversations with timestamps are available and needs for such technology are expected to increase in the future.

In contrast to the increase of surveillance cameras, the protection of privacy with respect to the use of video shot by the cameras has become a problem and is under discussion at the Ministry of Internal Affairs and Communications. Due to the enforcement of the Personal Information Protection Law, the use of personal information of individuals is strictly controlled, and the information has to be disclosed and/or partially deleted if the person requests.

To address the problem of achieving reliability in terms of evidence as well as protecting privacy, research has been progressed on a partial guarantee of the originality of a part of an electronic document and sanitizing signature technology for concealment. In particular, Japanese Patent Application No. 2006-528342, for example, discloses a sanitizing signature technology for electronic documents addressing the problem that a signature applied to a document cannot be verified due to the concealment of a part of the document. Specifically, a method is disclosed in which the content of an electronic document is divided into items, summary data are calculated for each item, and a digital signature is appended to the summary data of the items. The summary data correspond to hash data calculated by a cryptographic one-way hash function and are referred to as a message digest.

This technology enables signature verification even if an electronic document with a signature has been sanitized, and enables third-party certification that no change has been made other than the portions sanitized, changed, and/or added for concealment. This technology is applicable to video/audio data, and Japanese Laid-Open Patent Publication No. 2009-152713, for example, discloses a technology to guarantee the originality of video data and to extract data from a signature subject enabling protection of privacy.

However, if applied to video data recorded in real-time and over a long period, the conventional arts described above cannot certify the originality of video data recorded before the recording stops due to an error, such as a forced powering off of the video recording device.

From the viewpoint of a user who installs the surveillance camera, since important evidence can be included in the video recorded by then, it is desirable for recorded data to be stored with respective certifications. However, it is not until a digital signature functioning as certification is appended through a formal procedure (for example, when the recording stop button is pushed) that the third-party certification for the originality of the video data by the digital signature appended thereto is enabled. When an error occurs, the digital signature process cannot be performed and thus, the third-party certification that falsification has not occurred is also impossible.

As a result, the recorded video and message digests functioning as an indicator of falsification cannot certify that falsification has not occurred. In particular, a countermeasure is necessary for surveillance cameras operating 24 hours a day for 365 days a year, since a forced termination due to power outage, etc., cannot be completely prevented and thus, when the recording will be forcibly terminated cannot be predicted.

Regarding the problem described above, if the video is recorded at, for example, 30 frames per second (fps), 300 frames recorded in 10 seconds may be treated as a unit of guarantee. In this case, even if the recording stops due to an error, the video data recorded up until then can be certified against falsification.

However, in this case, only certification in 300-frame units is possible. It cannot be guaranteed that frames are temporally continuous over blocks, in other words, no malicious/accidental and unauthorized replacement and/or intermediate removal has occurred.

SUMMARY

According to an aspect of an embodiment, a signature generating device includes a receiving unit configured to receive a sequence of data; a summary data generating unit configured to sequentially generate summary data of the data upon reception of each of the data by the receiving unit; an obtaining unit configured to sequentially obtain, when the number of data included in a sequence of the summary data generated by the summary data generating unit reaches a given number, the sequence of the summary data as a block; a setting unit configured to set, as a signature subject, a current block constituted by the sequence of the summary data, and the summary data selected from at least one block contiguous to the current block; a digital signature generating unit configured to generate a digital signature concerning data summarized for the current block; and a sending unit configured to send the generated digital signature, the signature subject associated with the digital signature, and the data summarized for the current block.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 4 depicts a functional configuration of a video extracting device 105.

FIG. 5 depicts a functional configuration of a signature verifying device 107.

FIG. 18 is a flowchart of registration of a public key of the digital signature between a sending device and the CA device 102.

FIG. 19 is a flowchart of the communication of data having digital signatures and the verification by the receiving device.

FIGS. 20A and 20B are flowcharts of generation of the original video and of the signature.

FIG. 21 is a flowchart of the signature generation with respect to frame digests.

FIGS. 22A and 22B are flowcharts of the generation of the extracted video and of the signature.

FIG. 23 is a flowchart of the signature verification for the original video.

FIG. 24 is a flowchart of an acquisition of the extracted video.

DESCRIPTION OF EMBODIMENTS

Preferred embodiments of the present invention will be explained with reference to the accompanying drawings.

Figure 1:
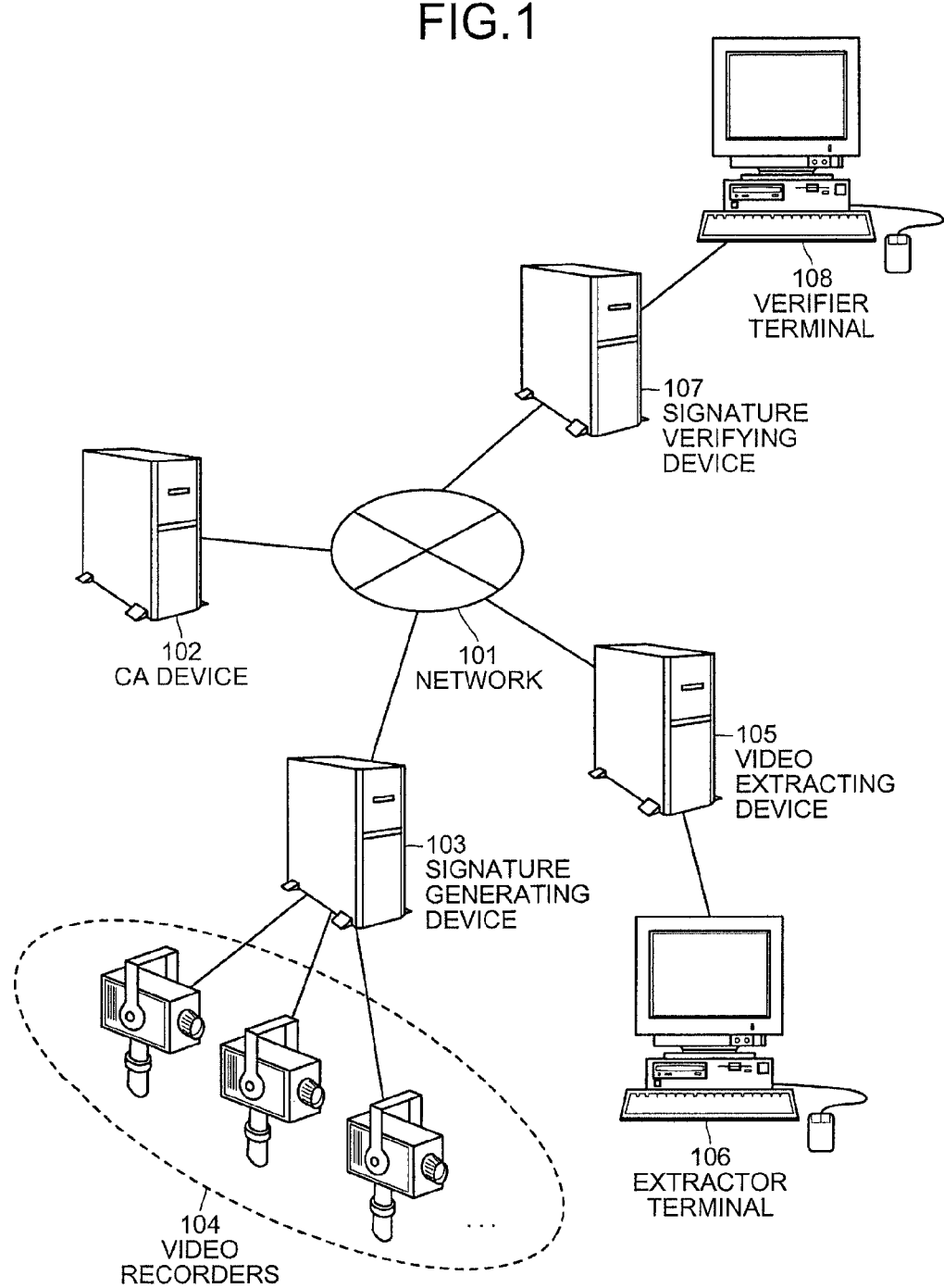
FIG. 1 depicts a configuration of a system according to an embodiment.

FIG. 1 depicts a configuration of a system according to an embodiment. The system includes a certificate authority (CA) device 102, a signature generating device 103, a video extracting device 105, and a signature verifying device 107. The system is connectable to a network 101. The signature generating device 103 is connected to video recorders 104. The video extracting device 105 is connected to an extractor terminal 106. The signature verifying device 107 is connected to a verifier terminal 108.

The network 101 can be any communication network such as the Internet, an intranet, and a wide area network. The CA device 102 is a server of a certificate authority that manages digital signature data. The digital signature is an encryption of summary data for a signature subject encrypted by a secret key stored in a sending device. The sending device sends the digital signature, the signature subject, and a public key certificate to a receiving device. The receiving device checks the validity of the public key certificate, decodes the encrypted digital signature by a public key included in the public key certificate, and compares it to the summary data obtained from the signature subject to determine whether the transmission is from an authorized sender. Details will be described with reference to FIG. 19.

The summary data are hash data calculated by a cryptographic one-way hash function with respect to the signature subject, and also are referred to as a message digest since they can reduce the size of the signature subject. The hash data generated by the function are unique and cannot be generated from other signature subjects, nor can the original data be restored therefrom.

Thus, the summary data are frequently used for data encryption and/or generation of a digital signature. Algorithms such as MD5, SHA-1, and SHA-256 are known functions. A hash generation algorithm (that is, which algorithm is used for generation of the summary data) is described in the public key certificate.

The signature generating device 103 is a server that stores data sent from the video recorders 104 and performs signature generation. The video recorders 104 are terminals that shoot and record original streaming data (hereinafter, "original video") to be subject to digital signature, and for example, are business surveillance cameras. The video recorders 104 can communicate with the signature generating device 103.

The video extracting device 105 stores data sent from the signature generating device 103 and data sent to the signature verifying device 107. The video extracting device 105 is operated through the extractor terminal 106, but may be directly operated through a mouse, keyboard, and/or display connected thereto. The extractor terminal 106 is a terminal for operating the video extracting device 105. The extractor terminal 106 can communicate with the video extracting device 105.

The signature verifying device 107 is a server that stores data sent from the video extracting device 105 and verifies the digital signature appended thereto. The signature verifying device 107 is operated through the verifier terminal 108, but may be directly operated through a mouse, keyboard, and/or display connected thereto. The verifier terminal 108 is a terminal for operating the signature verifying device 107. The verifier terminal 108 can communicate with the signature verifying device 107.

Figure 2:
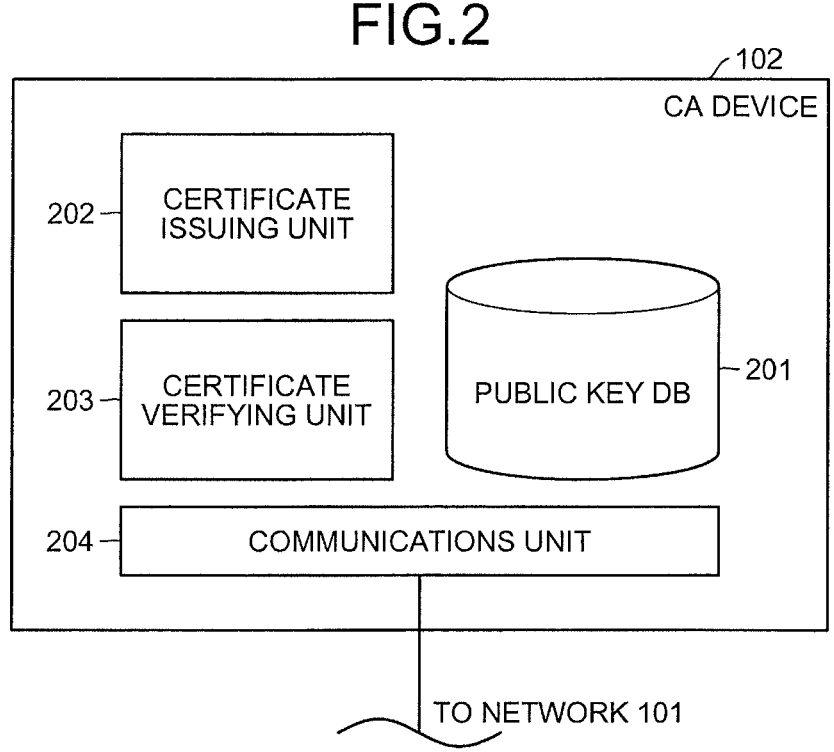
FIG. 2 depicts a functional configuration of a certificate authority (CA) device 102.

FIG. 2 depicts a functional configuration of the CA device 102. The CA device 102 includes a public key database (DB) 201, a certificate issuing unit 202, a certificate verifying unit 203, and a communications unit 204. The public key DB 201 stores public keys of the video recorders 104 and the extractor terminal 106. The certificate issuing unit 202 issues a public key certificate upon request. The certificate verifying unit 203 verifies the public key certificate. The communications unit 204 is connected to the network 101, and performs communications via the network 101.

Figure 3:
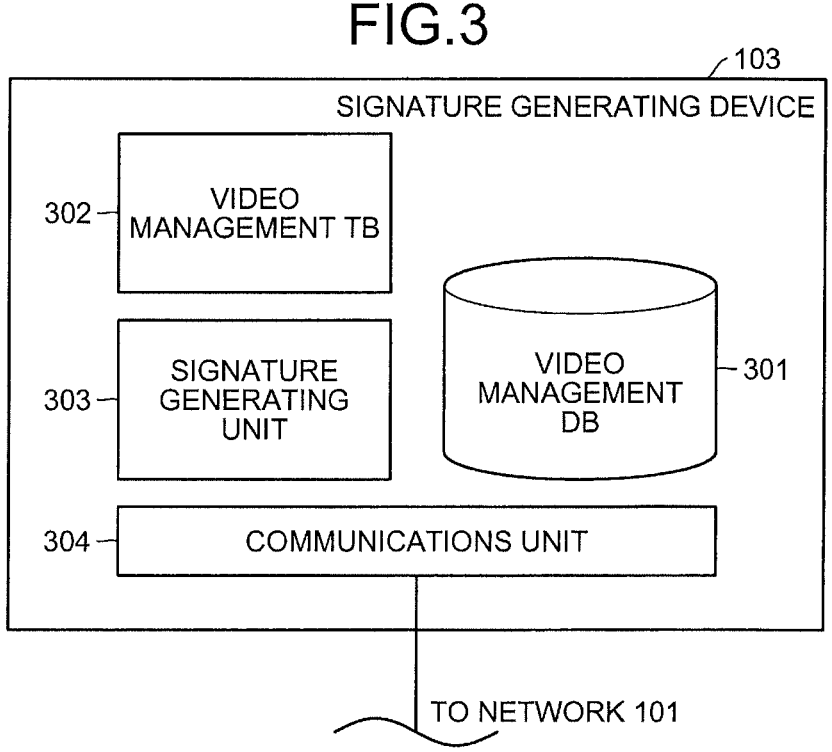
FIG. 3 depicts a functional configuration of a signature generating device 103.

FIG. 3 depicts a functional configuration of the signature generating device 103. The signature generating device 103 includes a video management DB 301, a video management table (TB) 302, a signature generating unit 303, and a communications unit 304. The video management DB 301 stores data sent from the video recorders 104 and data sent to the video extracting device 105. The video management TB 302 is a table for managing access control to the video management DB 301. The signature generating unit 303 appends digital signature(s) and signature subject(s) thereof to video data. The function of the signature generating unit 303 will be described with reference to FIG. 7. The communications unit 304 is connected to the network 101, and performs communication via the network 101.

FIG. 4 depicts a functional configuration of the video extracting device 105. The video extracting device 105 includes a video management DB 401, a video management TB 402, a signature generating unit 403, a signature verifying unit 404, and a communications unit 405. The video management DB 401 stores data sent from the signature generating device 103. The video management TB 402 is a table for managing access control to the video management DB 401. The signature generating unit 403 appends signature data to a video. The signature verifying unit 404 verifies signature data appended to the data sent from the signature generating device 103. The communications unit 405 is connected to the network 101, and performs communications via the network 101.

FIG. 5 depicts a functional configuration of the signature verifying device 107. The signature verifying device 107 includes a video management DB 501, a video management TB 502, a signature verifying unit 503, and a communications unit 504. The video management DB 501 stores data sent from the video extracting device 105. The video management TB 502 is a table for managing access control to the video management DB 501. The signature verifying unit 503 verifies signature data appended to the data sent from the video extracting device 105. The communications unit 504 is connected to the network 101, and performs communications via the network 101.

The signature generating device 103 is connected to the network 101 as described above, but can be operated offline. For example, the CA device 102 generates and writes public key certificates into removable media such as a flexible disk and a compact disk (CD), and the signature generating device 103 reads out the public key certificates through a magnetic disk drive 604 and an optical disk drive 606 of FIG. 6 described later. Similarly, video data are stored into a storage device of the signature generating device 103 after a digital signature has been appended thereto and are periodically written onto removable media, and the video extracting device 105 reads out the video data and the digital signature from the removable media.

Figure 6:
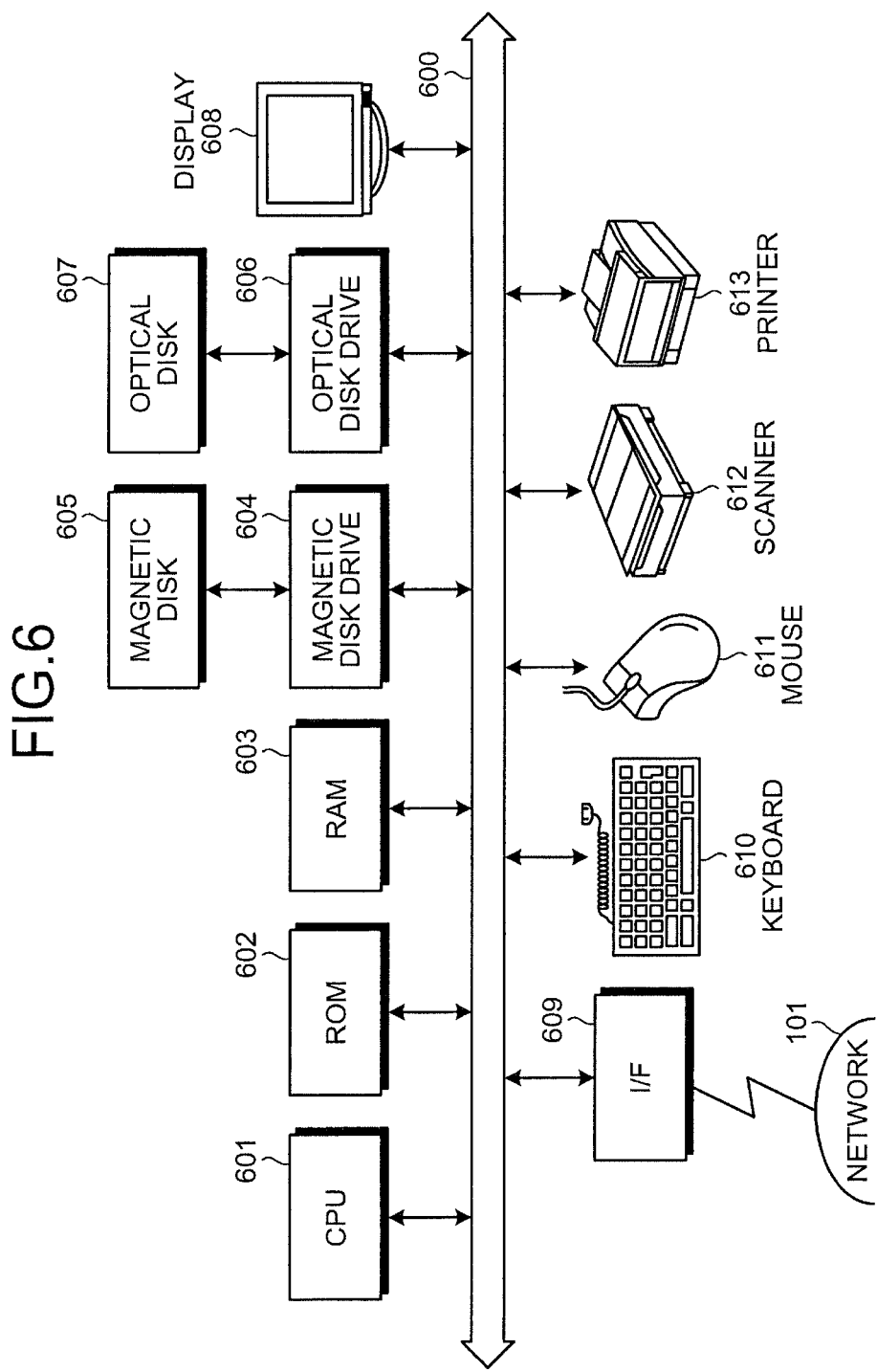
FIG. 6 is a block diagram of a hardware configuration of the signature generating device 103 according to the embodiments.

FIG. 6 is a block diagram of a hardware configuration of a signature generating device 103 according to the embodiments. As depicted in FIG. 6, the signature generating device 103 includes a central processing unit (CPU) 601, a read-only memory (ROM) 602, a random access memory (RAM) 603, a magnetic disk drive 604, a magnetic disk 605, an optical disk drive 606, an optical disk 607, a display 608, an interface (I/F) 609, a keyboard 610, a mouse 611, a scanner 612, and a printer 613, respectively connected by a bus 600.

The CPU 601 governs overall control of the signature generating device 103. The ROM 602 stores therein programs such as a boot program. The RAM 603 is used as a work area of the CPU 601. The magnetic disk drive 604, under the control of the CPU 601, controls the reading and writing of data with respect to the magnetic disk 605. The magnetic disk 605 stores therein data written under control of the magnetic disk drive 604.

The optical disk drive 606, under the control of the CPU 601, controls the reading and writing of data with respect to the optical disk 607. The optical disk 607 stores therein data written under control of the optical disk drive 606, the data being read by a computer.

The display 608 displays, for example, data such as text, images, functional information, etc., in addition to a cursor, icons, and/or tool boxes. A cathode ray tube (CRT), a thin-film-transistor (TFT) liquid crystal display, a plasma display, etc., may be employed as the display 608.

The I/F 609 is connected to other apparatuses through the network 101. The I/F 609 administers an internal interface with the network 101 and controls the input/output of data from/to external apparatuses. For example, a modem or a LAN adaptor may be employed as the I/F 609.

The keyboard 610 includes, for example, keys for inputting letters, numerals, and various instructions and performs the input of data. Alternatively, a touch-panel-type input pad or numeric keypad, etc. may be adopted. The mouse 611 is used to move the cursor, select a region, or move and change the size of windows. A track ball or a joy stick may be adopted provided each respectively has a function similar to a pointing device.

The scanner 612 optically reads an image and takes in the image data into the signature generating device 103. The scanner 612 may have an optical character reader (OCR) function as well. The printer 613 prints image data and text data. The printer 613 may be, for example, a laser printer or an ink jet printer.

The signature verifying device 107 has a similar hardware configuration to the signature generating device 103 and includes a CPU, a ROM, a RAM, a magnetic disk drive, a magnetic disk, an optical disk drive, an optical disk, a display, an I/F, a keyboard, a mouse, a scanner, and a printer.

Figure 7:
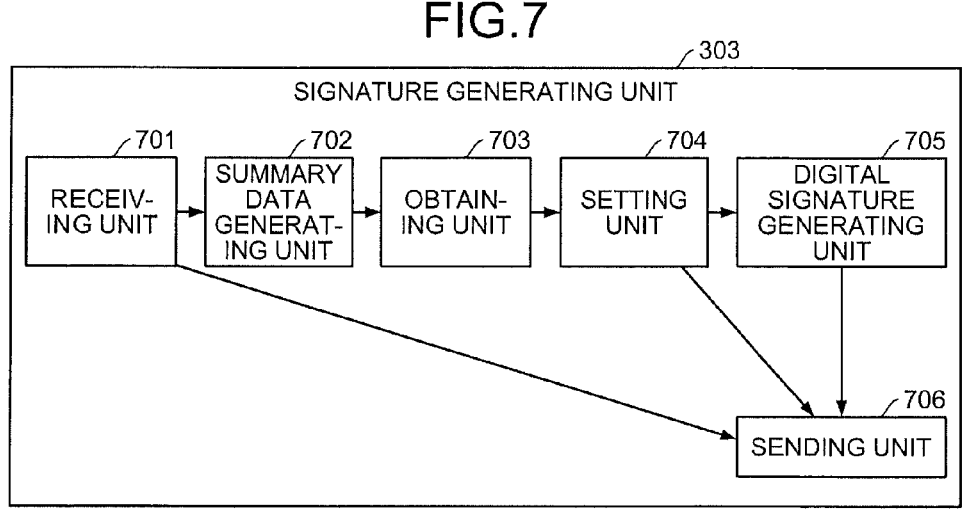
FIG. 7 depicts a functional configuration of a signature generating unit 303 in the signature generating device 103.

FIG. 7 depicts a functional configuration of the signature generating unit 303 in the signature generating device 103. The signature generating unit 303 includes a receiving unit 701, a summary data generating unit 702, an obtaining unit 703, a setting unit 704, a digital signature generating unit 705, and a sending unit 706. These functions (the receiving unit 701 to the sending unit 706), as a controller, are implemented by, for example, causing the CPU 601 or another CPU via the I/F 609 to execute a program stored in a storage device such as the ROM 602, the RAM 603, the magnetic disk 605, and the optical disk 607 depicted in FIG. 6.

The receiving unit 701 continuously receives video data from the video recorders 104. For example, if the video is recorded at 30 fps, the receiving unit 701 receives 30 frames per second from the video recorder 104. The extracted data are stored in a storage device such as the RAM 603, the magnetic disk 605, and the optical disk 607.

The summary data generating unit 702 sequentially generates summary data of frame data (for example, digests of frames) with respect to frames received by the receiving unit 701. For example, the digest is a result of substituting a frame into a hash function as an argument. Hereinafter, the digest of a frame is referred to as "frame digest." A verifier can easily find a falsification of the content of the frame since it changes the result of the hash function. The result of the generation is stored in a storage device such as the RAM 603, the magnetic disk 605, and the optical disk 607.

The obtaining unit 703 obtains a sequence of frame digests as one block when the number of frame digests generated by the summary data generating unit 702 reaches a given number.

For example, when the signature generating device 103 has sequentially received video data and generated frame digests for 300 frames, the frame digests of frames 1 to 300 are treated as one block. Subsequently, when frames 301 to 600 are sequentially received and the frame digests are generated, the frame digests of 300 frames (frames 301 to 600) are treated as one block. If the recording is stopped after frame 756 is received, 156 frames (frames 601 to 756) become one block. The obtained blocks are stored in a storage device such as the RAM 603, the magnetic disk 605, and the optical disk 607.

The setting unit 704, with respect to each block obtained by the obtaining unit 703, sets the frame digests included in the block and an arbitral frame digest(s) included in at least one of the blocks contiguous to the block (i.e., the preceding block and/or the next block) as a subject of digital signature (hereinafter, "signature subject"). The preceding and/or next block(s) may be the preceding one block, the next one block, or both the preceding block and the next block, and the frame digests thereof and of the obtained block may be set as the signature subject. The frame digest of the next block may be the first-generated frame digest in the next block.

If the obtained block is the head block among all blocks, an identifier indicating the start of the video data (hereinafter, "start ID") may be included into the signature subject. Similarly, if the obtained block is the end block among all blocks, an identifier indicating the end of the video data (hereinafter, "end ID") may be included into the signature subject.

For example, with respect to the block constituted by the frame digests of frames 301 to 600, the frame digests of frame 300 of the preceding block and frame 601 of the next block are included into the signature subject. The block of frames 1 to 300 includes a character string such as "START" as the start ID. The block of frames 601 to 756 (the recording is stopped after frame 756 is received) includes a character string such as "NULL" as the end ID. The signature subject is stored in a storage device such as the RAM 603, the magnetic disk 605, and the optical disk 607.

The digital signature generating unit 705 generates a digital signature of the video data summarized by the block set as the signature subject by the setting unit 704. With respect to the block of frames 301 to 600 obtained by the obtaining unit 703, for example, a signature subject that includes the frame digests of frames 300 and 601 is set by the setting unit 704 and the signature generating device 103 generates a digital signature with respect to the set signature subject.

For example, the signature generating device 103 generates hash data from the signature subject by a hash function, and generates the digital signature from the hash data by a previously-[R]preliminarily generated secret key. The digital signature encrypted by the secret key is restored to the hash data by the public key. Thus, a third party can verify the obtained signature subject and digital signature since the hash data generated from the signature subject by the hash function match the hash data decoded from the digital signature by the public key. The generated digital signature is stored in a storage device such as the RAM 603, the magnetic disk 605, and the optical disk 607.

The sending unit 706 correlates and sends to a storage device, the video data received by the receiving unit 701, the signature subject set by the setting unit 704, and the digital signature generated by the digital signature generating unit 705. The signature subject and the digital signature are collectively called as "signature data." For example, the sending unit 706 sends the video data of frames 301 to 600, the frame digests of frames 300 to 601, and the digital signature with respect to the frame digests. The result of the calculation may be stored in a storage device such as the RAM 603, the magnetic disk 605, and the optical disk 607.

The signature generating unit 403 in the video extracting device 105 has a function similar to that of the signature generating unit 303 described above. The signature generating unit 403 may generate a digital signature with respect to a part of the received video data (for example, apply the digital signature to frames 200 to 550 among frames 1 to 756). Details will be described with reference to FIG. 13.

Figure 8:
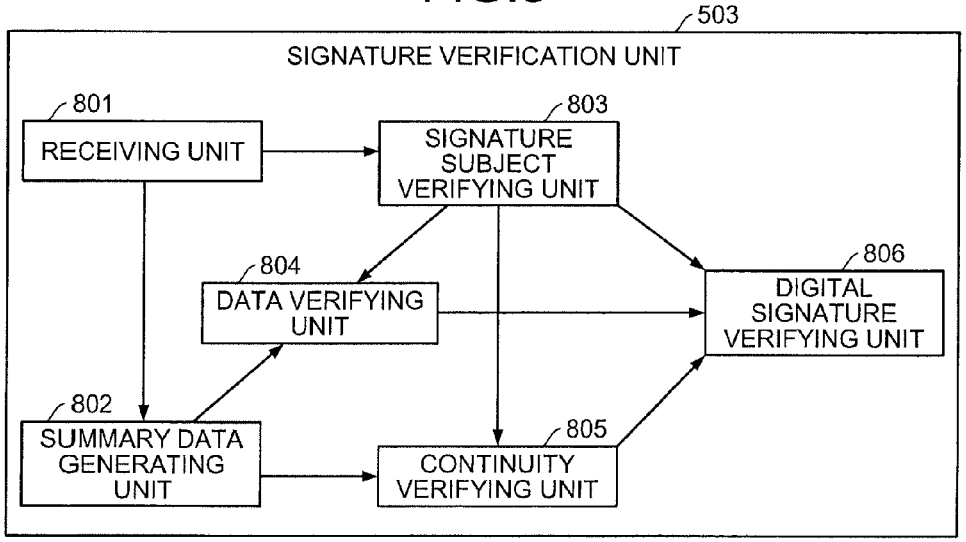
FIG. 8 depicts a functional configuration of a signature verifying unit 503 in the signature verifying device 107.

FIG. 8 depicts a functional configuration of the signature verifying unit 503 in the signature verifying device 107. The signature verifying unit 503 includes a receiving unit 801, a summary data generating unit 802, a signature subject verifying unit 803, a data verifying unit 804, a continuity verifying unit 805, and a digital signature verifying unit 806. These functions (the receiving unit 801 to the digital signature verifying unit 806), as a controller, are implemented by, for example, causing the CPU of the signature verifying device 107 or another CPU via the I/F to execute a program stored in a storage device of the signature verifying device 107 such as the ROM, the RAM, the magnetic disk, and the optical disk.

The receiving unit 801 receives the video data, the signature subjects each of which is a block of a given number of frame digests (that is an example of the summary data of the frames of the video data), and the digital signatures with respect to the signature subjects. Each signature subject includes the frame digests of the block and the frame digest(s) selected from at least one of the blocks contiguous to the block (i.e., the preceding block and/or the next block). The preceding and/or next block(s) may be the next one block, the preceding one block, or both the preceding and the next blocks.

A signature subject may include the frame digests of the block and the start ID or the end ID. The received data are stored in a storage device of the signature verifying device 107 such as the RAM, the magnetic disk, and the optical disk.

For example, the video data includes frames 1 to 756. The signature subject includes two blocks (i.e., the preceding block and the next block), the start ID, and the end ID.

In this example, there are three pairs of the signature subject and the digital signature. The first signature subject includes the start ID such as a character string "START" and the frame digests of frames 1 to 301, and the digital signature is generated with respect to the signature subject. The second signature subject includes the frame digests of frames 300 to 601, and the digital signature is generated with respect to the signature subject. The third signature subject includes the frame digests of frames 600 to 756 and the end ID such as a character string "NULL," and the digital signature is generated with respect to the signature subject. Details will be described with reference to FIG. 12.

The summary data generating unit 802 generates summary data of frame data (for example, frame digests) with respect to the frames received by the receiving unit 801. The summary data generating unit 802 has a similar function to that of the summary data generating unit 702. The received data are stored in a storage device of the signature verifying device 107 such as the RAM, the magnetic disk, and the optical disk.

The signature subject verifying unit 803 verifies the integrity of the signature subject received by the receiving unit 801, based on the received digital signature. The second signature subject and digital signature described above are taken as an example. The signature verifying device 107 calculates the summary data (for example, the hash value) with respect to the signature subject, and if the calculated value matches a value decoded from the digital signature by the public key, the integrity of the signature subject is guaranteed. The result of the verification is stored in a storage device of the signature verifying device 107 such the RAM, the magnetic disk, and the optical disk.

The data verifying unit 804 verifies the integrity of a sequence of data received by the receiving unit 801, based on the frame digest generated by the summary data generating unit 802 and the signature subject verified by the signature subject verifying unit 803. The second signature subject and digital signature described above are taken as an example. The frame digests calculated with respect to the sequence of data (in this example, frames 301 to 600) are compared to the values of frames 301 to 600 included in the signature subject. If the values match, the integrity of each frame can be guaranteed. The result of the verification is stored in a storage device of the signature verifying device 107 such as the RAM, the magnetic disk, and the optical disk.

The continuity verifying unit 805 verifies the integrity concerning the continuity of the blocks received by the receiving unit 801, based on the frame digest generated by the summary data generating unit 802 and the signature subject verified by the signature subject verifying unit 803. The result of the verification is stored in a storage device of the signature verifying device 107 such as the RAM, the magnetic disk, and the optical disk. The second signature subject and digital signature described above are taken as an example.

The second signature subject includes the frame digest of frame 300 also included in the first block. The frame digest of frame 300 included in the second signature subject is compared to the frame digest generated by the summary data generating unit 802 with respect to frame 300 received by the receiving unit 801. If the digests match, it can be guaranteed that the second signature subject follows the first signature subject. Similarly, the second signature subject includes the frame digest of frame 601 also included in the third block. Through a similar operation, it can be guaranteed that the second signature subject is followed by the third signature subject.

The first signature subject also includes the start ID such as a character string "START" and thus, it can be guaranteed that the first signature subject is the head block among the blocks. The third signature subject also includes the end ID such as a character string "NULL" and thus, it can be guaranteed that the third signature subject is the end block among the blocks.

The digital signature verifying unit 806 verifies the integrity of the video data, the signature subject, and the digital signature received by the receiving unit 801, based on the results of verifications performed by the signature subject verifying unit 803, the data verifying unit 804, and the continuity verifying unit 805. The integrity can be guaranteed if, for example, all of the verifications are successful. The result of the verification is stored in a storage device of the signature verifying device 107 such as the RAM, the magnetic disk, and the optical disk.

The signature verifying unit 404 in the video extracting device 105 has a similar function to that of the signature verifying unit 503 described above. The signature verifying unit 503 may verify the integrity of a part extracted from the video data. For example, for frames 1 to 756, the integrity of frames 200 to 550 is verified using the video data appended with digital signatures. Details will be described with reference to FIG. 14.

Using the devices and terminals described above, processes performed in the system according to the embodiment are described. According to process task, the devices and the terminals in the embodiment can act as the signing device, the extracting device, or the verifying device. The signing device guarantees the content of original video by appending a signature of the video recorder 104. The signature may be a digital signature generated based on data concerning a manager of the video recorder 104.

The extracting device extracts a part of the original video to which the signature of the video recorder 104 is appended, and discloses the part to the verifying device as extracted video. There are two types of extraction, namely, an onymous extraction in which data concerning the extracting device is also disclosed to indicate which device performs the extraction, and an anonymous extraction in which the extracting device performs the extraction anonymously. In the embodiment, it is assumed that the onymous extraction is performed.

The verifying device verifies whether the disclosed extracted video is guaranteed by the video recorder 104. Specifically, the verifying device verifies that the extracted video is a part of the original video to which the video recorder 104 applied the signature, and the extraction thereof is performed by the extracting device. The digital signature is processed by each device according to procedures that will be described with reference to FIGS. 18 and 19.

Figure 9:
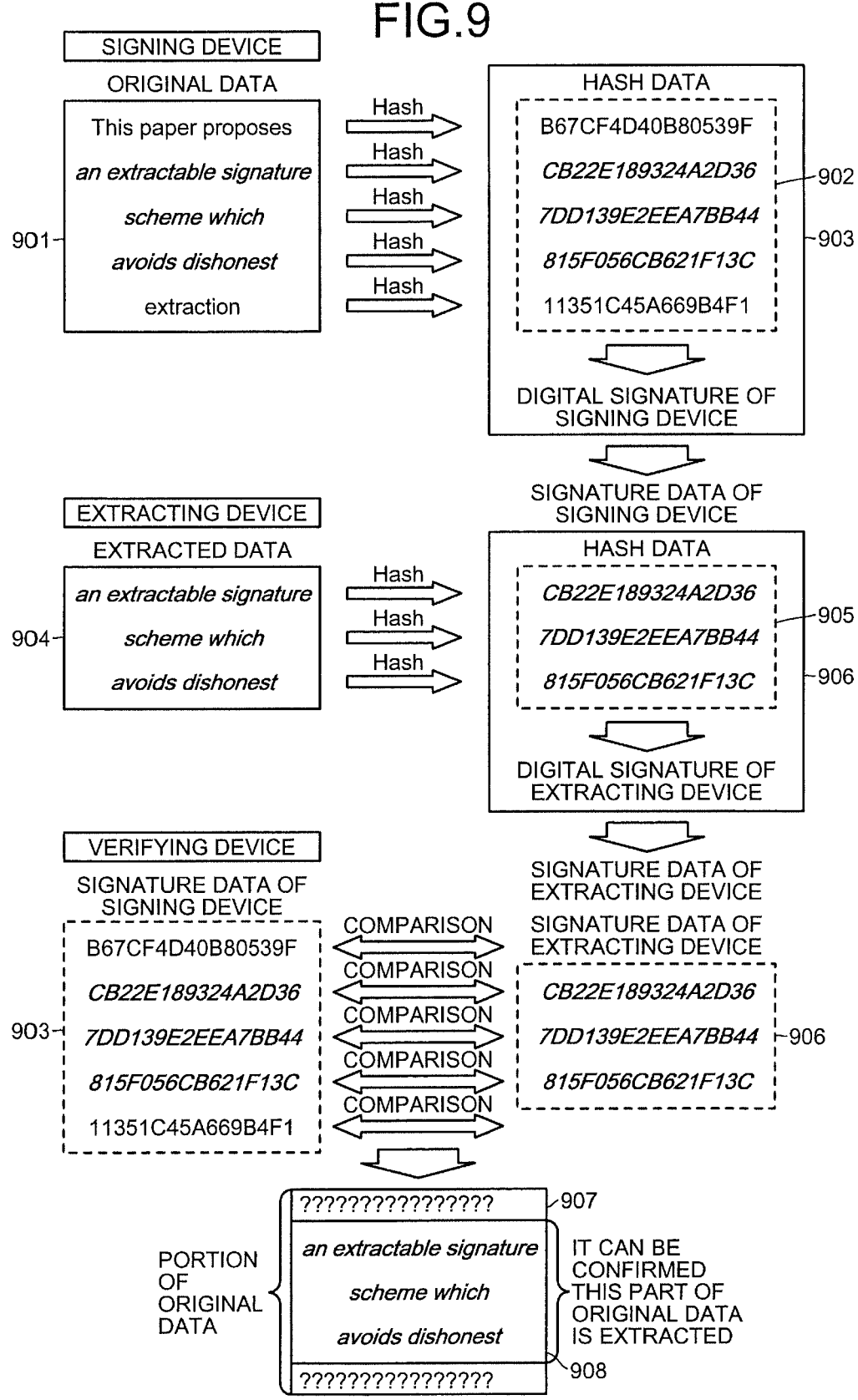
FIG. 9 depicts an overview of a signature algorithm.

FIG. 9 depicts an overview of a signature algorithm. The signing device divides original data 901 into components, calculates hash data of each component to generate hash data 902 as the signature subject, and appends the digital signature of the signing device to the signature subject. The hash data 902 and the digital signature constitute signature data 903 of the signing device.

The extracting device extracts the component(s) as extracted data 904 from the data to which the signature data of the signing device are appended, and through a similar operation to that of the signing device, appends the digital signature of the extracting device to hash data 905 constituting the signature subject. The hash data 905 and the digital signature constitute signature data 906 of the extracting device.

The verifying device verifies the integrity of the hash data 902, based on the digital signature of the signing device included in the signature data 903. Similarly, the verifying device verifies the integrity of the hash data 905, based on the digital signature of the extracting device included in the signature data 906. The verifying device further generates hash data from the disclosed component(s), and verifies that they are identical to the hash data 905. Finally, the verifying device compares the hash data of the signing device and those of the extracting device, to determine that a portion 908 corresponding to the hash data of the extracting device is a portion 907 of the original data. On the other hand, the component(s) have been falsified if the hash data of the extracted data 904 do not include the hash data of the original data 901.

Figure 10:
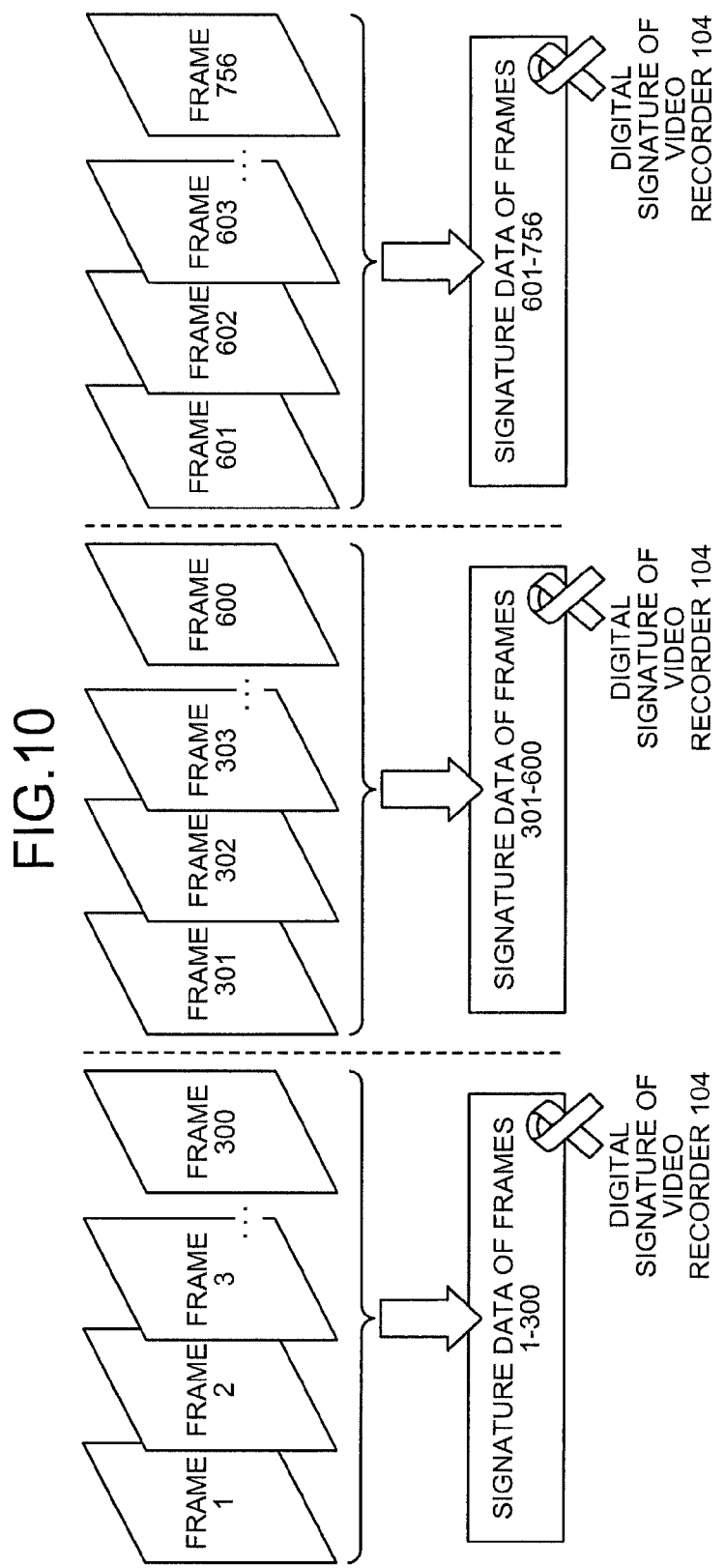
FIG. 10 depicts an overview of signature generation for original video (in the embodiment, streaming data).

FIG. 10 depicts an overview of signature generation for the original video (in the embodiment, streaming data). It is assumed that data for one screen constitute one frame, the video recorder 104 records 30 frames per second (30 fps), and the signature generating device 103 appends the signature for every 300 frames recorded every 10 seconds.

The digital signature is appended to blocks of 300 frames such as frames 1 to 300, frames 301 to 600. However, for the last group such as frames 601 to 756, the digital signature is appended to 156 frames since the recording is stopped at frame 756 before reaching frame 900. The frames 1 to 756 to which the digital signatures are appended are called as "original video." For simplicity, a short video with frames 1 to 756 and of about 25 seconds is used in the embodiment. In actual operation, however, it is assumed that a surveillance camera records over a long period. Thus, actually, for a video of about 8 hours, about 864,000 frames are output and 2,880 digital signatures are generated.

Figure 11:
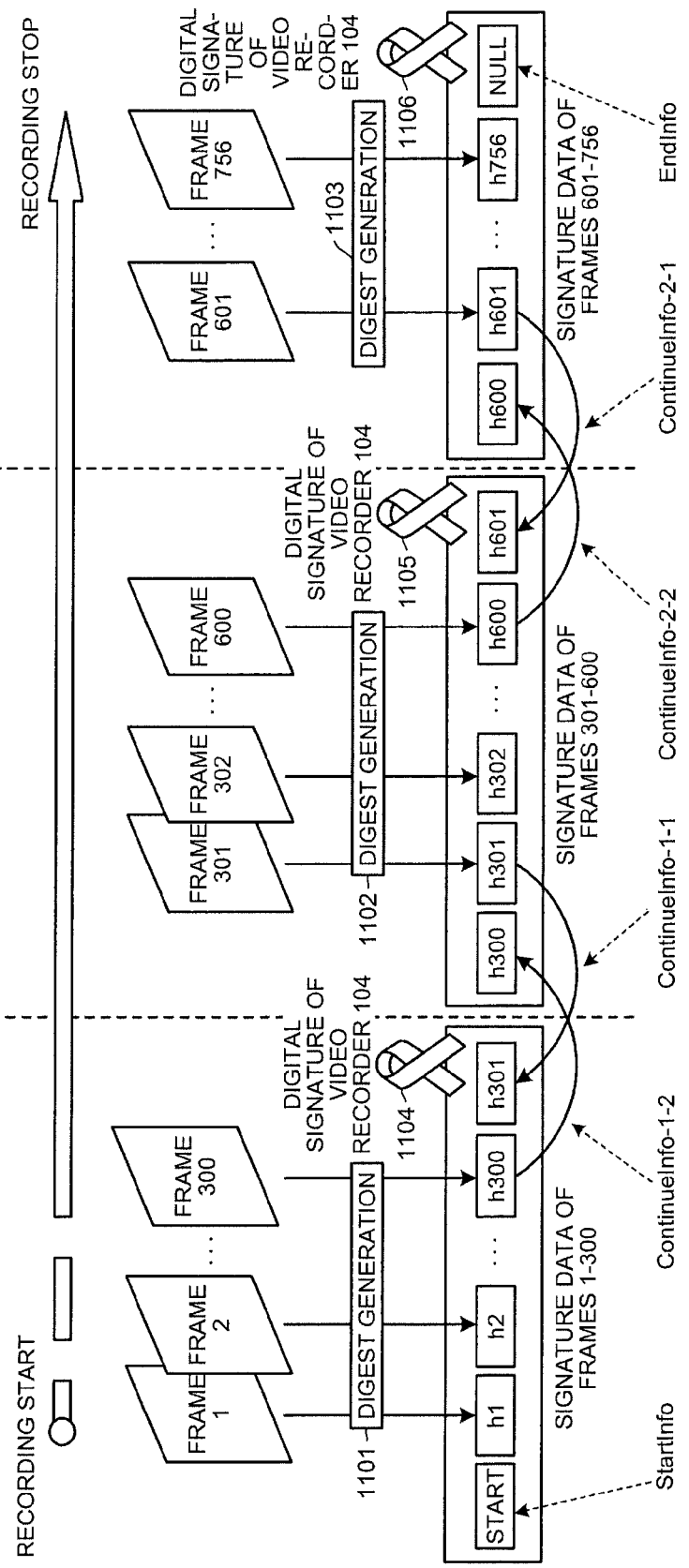
FIG. 11 depicts the signature generation for the original video.

FIG. 11 depicts the signature generation for the original video. The video recorder 104 starts frame recording. A recording start request is issued when, for example, a recording start button of the video recorder 104 is pushed. The recording may be automatically started upon powering-on.

The recorded frames are received by the signature generating device 103 that sequentially performs digest generation 1101. For the first block, the signature subject includes frame digests h1 to h300 of frames 1 to 300, the start ID such as "START" (denoted by "StartInfo"), and frame digest h301 of frame 301 (denoted by "ContinueInfo-1-1") to guarantee the continuity to the next block.

After generating frame digest h301, the signature generating device 103 generates a digital signature 1104 of the video recorder 104 by the secret key of the video recorder 104. The signature subject and the digital signature constitute the signature data of frames 1 to 300.

For the second block, the signature generating device 103 performs digest generation 1102 sequentially for frames 301 to 600. Frame digest h300 of frame 300 (denoted by "ContinueInfo-1-2") is then appended to the signature subject to guarantee the continuity from the signature data of frames 1 to 300. Similarly, frame digest h601 of frame 601 (denoted by "ContinueInfo-2-1") is appended to the signature subject to guarantee the continuity to the signature data of frame 601 and subsequent frames.

After generating frame digest h601, the signature generating device 103 generates a digital signature 1105 of the video recorder 104, using the secret key of the video recorder 104. The signature subject and the digital signature constitute the signature data of frames 301 to 600.

For the third block, the recording is stopped after frame 756 is recorded upon reception of a recording stop request by the video recorder 104. The request is issued when, for example, a recording stop button of the video recorder 104 is pushed.

The recorded frames are received by the signature generating device 103 that sequentially performs digest generation 1103. Frame digest h600 of frame 600 (denoted by "ContinueInfo-2-2") is then appended to the signature subject to guarantee the continuity from the signature data of frames 301 to 600. The end ID such as "NULL" (denoted by "EndInfo") is also appended to the signature subject.

Upon reception of a recording stop instruction, the signature generating device 103 generates a digital signature 1106 of the video recorder 104, using the secret key of the video recorder 104. The signature subject and the digital signature constitute the signature data of frames 601 to 756.

Figure 12:
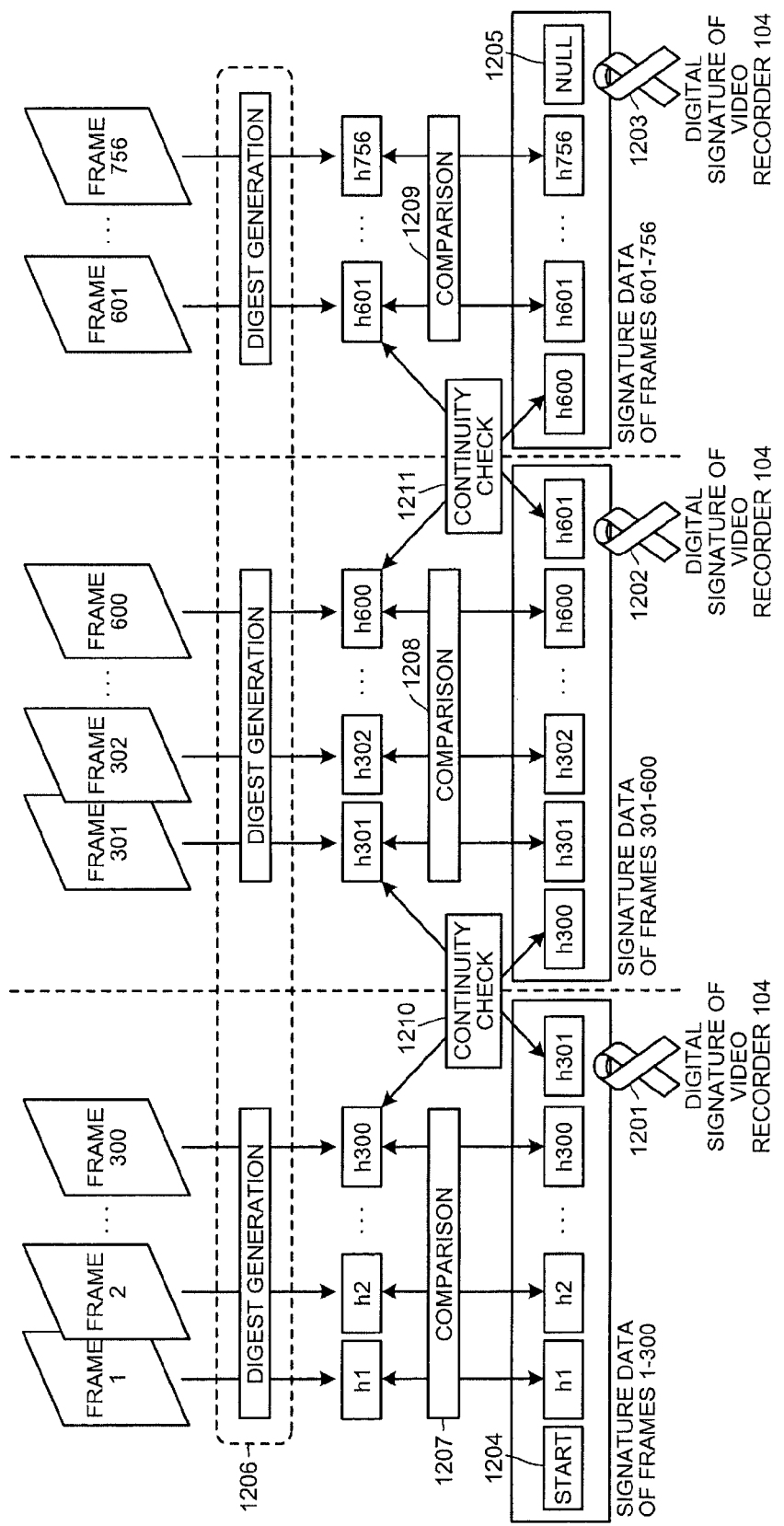
FIG. 12 depicts signature verification for the original video.

FIG. 12 depicts signature verification for the original video. The signature verifying device 107 receives the original video of frames 1 to 756, the signature data of frames 1 to 300, the signature data of frames 301 to 600, and the signature data of frames 601 to 756.

The integrity of each signature subject is verified first. For the first block, the signature verifying device 107 obtains from the signature data of frames 1 to 300, the signature subject and a digital signature 1201 of the video recorder 104 and verifies the integrity. Similarly, for the second block and the third block, the signature verifying device 107 verifies the integrity of the signature data of frames 301 to 600 and of frames 601 to 756 using digital signatures 1202 and 1203 of the video recorder 104, respectively.

If the signature data have not been falsified from the time of generation and thus, the integrity is confirmed, the signature verifying device 107 verifies whether the original video has been improperly cut. The signature verifying device 107 confirms that a head signature 1204 located at the beginning of the signature subject of the signature data of frames 1 to 300 is the start ID such as a character string "START," thereby checking the start of the original video.

Similarly, the signature verifying device 107 confirms that an end signature 1205 located at the end of the signature subject of the signature data of frames 601 to 756 is the end ID such as a character string "NULL," thereby checking the end of the original video.

The signature verifying device 107 generates, with respect to the original video, frame digests h1, h2, . . . , h756 for respective frames sequentially from frame 1 via digest generation 1206, and compares the generated frame digests h1 to h756 to the frame digests included in the signature subjects to verify the integrity of each frame.

For each block, the integrity of each of the frames is verified. For the first block, the integrity is verified through a comparison 1207 of the frame digests h1 to h300 as the signature subject of the signature data of frames 1 to 300 and the generated frame digests h1 to h300. Similarly, the integrity is verified through a comparison 1208 for frames 301 to 600 as the second block and a comparison 1209 for frames 601 to 756 as the third block.

Finally, the continuity of the blocks is verified. The signature data of frames 1 to 300 as the first block includes frame digest h301 of frame 301 included in the second block. The signature verifying device 107 performs a continuity check 1210 based on this frame digest h301 and frame digest h301 generated by the digest generation 1206. Thus, it can be guaranteed that the first block is followed by the second block.

Similarly, it can be guaranteed that the second block follows the first block by performing the continuity check 1210 based on frame digest h300 of frame 300 included in the second block.

A similar process is performed with respect to the second block and the third block. The signature verifying device 107 can guarantee that the second block is followed by the third block by performing a continuity check 1211 based on frame digest h601 of frame 601 included in the second block, and that the third block follows the second block by performing the continuity check 1211 based on frame digest h600 of frame 600 included in the third block.

Figure 13:
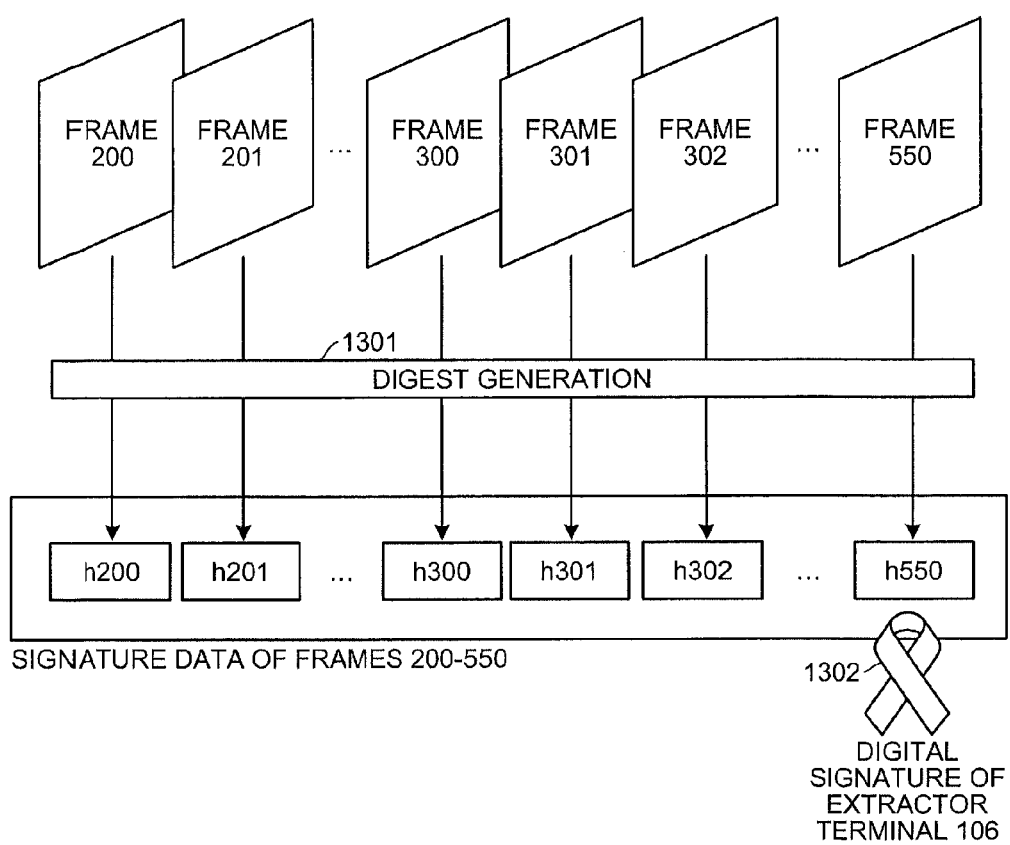
FIG. 13 depicts signature generation for extracted video.

FIG. 13 depicts signature generation for the extracted video. The signature generating unit 403 of the video extracting device 105 generates frame digests h200 to h550 based on the extracted frames 200 to 550 through a digest generation 1301. The frame digests h200 to h550 constitute the signature subject, and the signature generating unit 403 generates a digital signature 1302 of the extractor terminal 106, using the secret key of the extractor terminal 106 that has extracted frames 200 to 550.

In this example, the signature data is generated for the signature subject of 350 frames (frames 200 to 550). Depending on operation, however, the signature data may be generated and managed for 300 frames similar to the generation of signature data with respect to the original video. In this case, the signature data is generated for 300 frames, and then generated for 50 frames.

For a video format with inter-frame prediction such as the Moving Picture Experts Group (MPEG), data may be extracted from the beginning of the Group of Pictures (GOP) that is a minimum unit for display. In this case, the extracted video can be replayed from the beginning.

Figure 14:
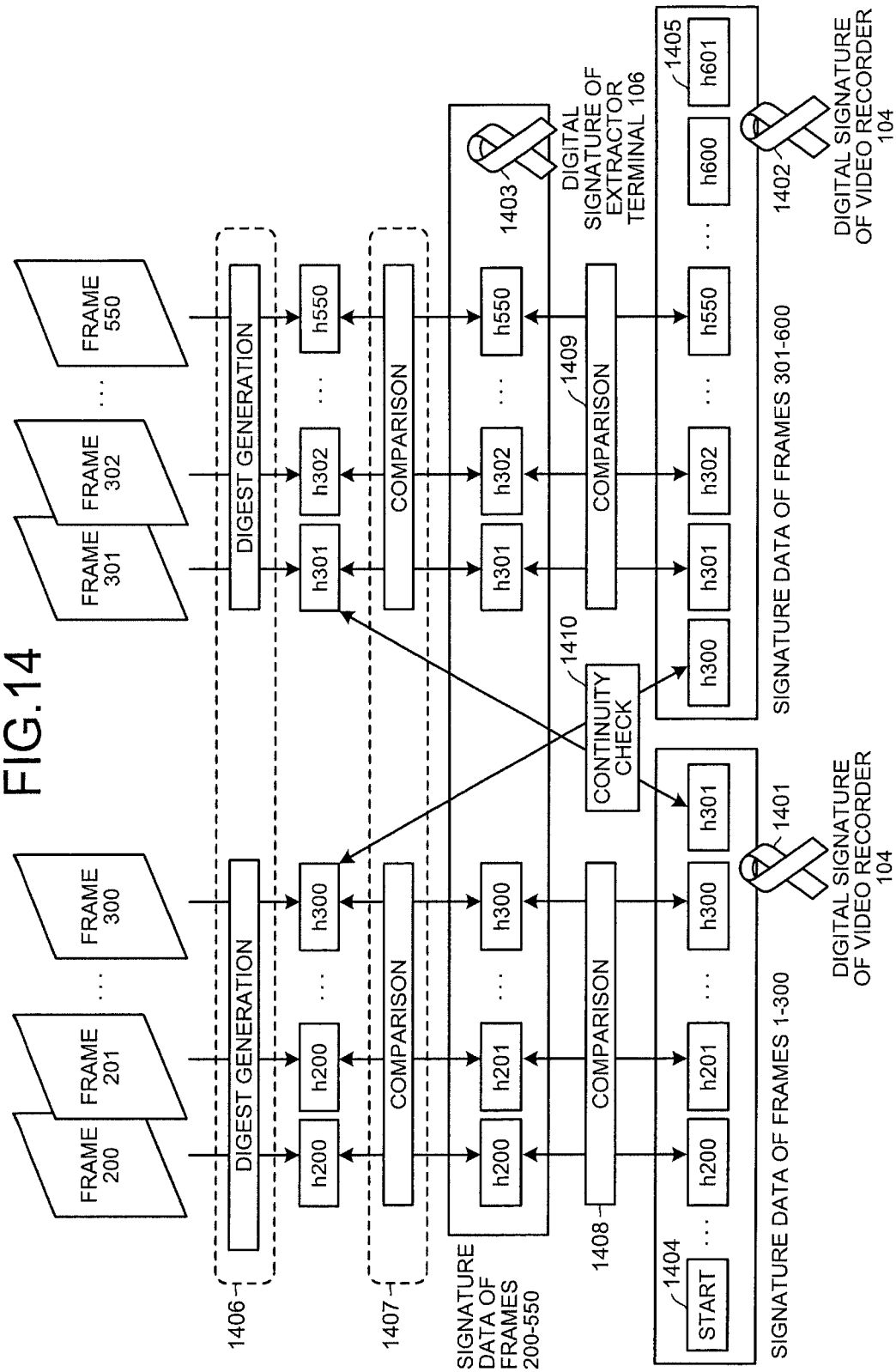
FIG. 14 depicts signature verification for the extracted video.

FIG. 14 depicts signature verification for the extracted video. The signature verifying device 107 receives the extracted video including frames 200 to 550, the signature data of frames 1 to 300, the signature data of frames 301 to 600, and the signature data of frames 200 to 550.

The integrity of each signature subject is verified first. For the first block, the signature verifying device 107 obtains the signature subject and a digital signature 1401 of the video recorder 104 from the signature data of frames 1 to 300, and verifies the integrity. Similarly, for the second block, the signature verifying device 107 verifies the integrity of the signature data of frames 301 to 600 using a digital signature 1402 of the video recorder 104. The signature verifying device 107 also verifies the integrity of the signature data of frames 200 to 550 using a digital signature 1403 of the extractor terminal 106.

If the signature data have not been falsified from the time of generation and thus, the integrity is confirmed, the signature verifying device 107 verifies whether the extracted video has been properly cut. In the verification, the start point can be identified by checking a head signature 1404 located at the beginning of the signature subject of the signature data of frames 1 to 300. The head signature 1404 of FIG. 14 is the start ID such as "START," by which the start point of extraction of the extracted video can be identified.

Similarly, the end point can be identified by checking an end signature 1405 located at the end of the signature subject of the signature data of frames 301 to 600. The end signature 1405 of FIG. 14 is not the end ID such as "NULL," but frame digest h601 of frame 601 indicating the presence of subsequent digital signature(s).

The signature verifying device 107 re-generates frame digests sequentially from frame 200 through digest generation 1406, and performs a comparison 1407 of the generated frame digests and corresponding frame digests recorded in the signature data of frames 200 to 550. By the comparison 1407, it can be guaranteed that each frame of the extracted video has not been falsified from the time of extraction.

A comparison 1408 is performed with respect to frame digests h200 to h300 included in the signature data of frames 200 to 550 and frame digests h200 to h300 included in the signature data of frames 1 to 300. Similarly, a comparison 1409 is performed with respect to frame digests h301 to h550 included in the signature data of frames 200 to 550 and frame digests h301 to h550 included in the signature data of frames 301 to 600.

By the processes up to the comparison 1409, it can be guaranteed that each frame of the extracted video has not been falsified since the generation of the original video, and is identical to the corresponding part of the original video.

Finally, the continuity of the blocks for the extracted video is verified. The signature data of frames 1 to 300 as the first block includes frame digest h301 of frame 301. The signature verifying device 107 performs a continuity check 1410 with respect to this frame digest h301 and frame digest h301 generated by the digest generation 1406.

Similarly, the signature data of frames 301 to 600 as the second block includes frame digest h300 of frame 300. The signature verifying device 107 performs the continuity check 1410 with respect to this frame digest h300 and frame digest h300 generated by the digest generation 1406.

If all of the verifications are successful, the continuity of the signature data divided into pieces can be confirmed. By the comparison of frame digests, it can be also confirmed that frames 200 to 550 constituting the extracted video are part of frames 1 to 756 constituting the original video, and have not been changed from the time of generation of the original video.

Figure 15:
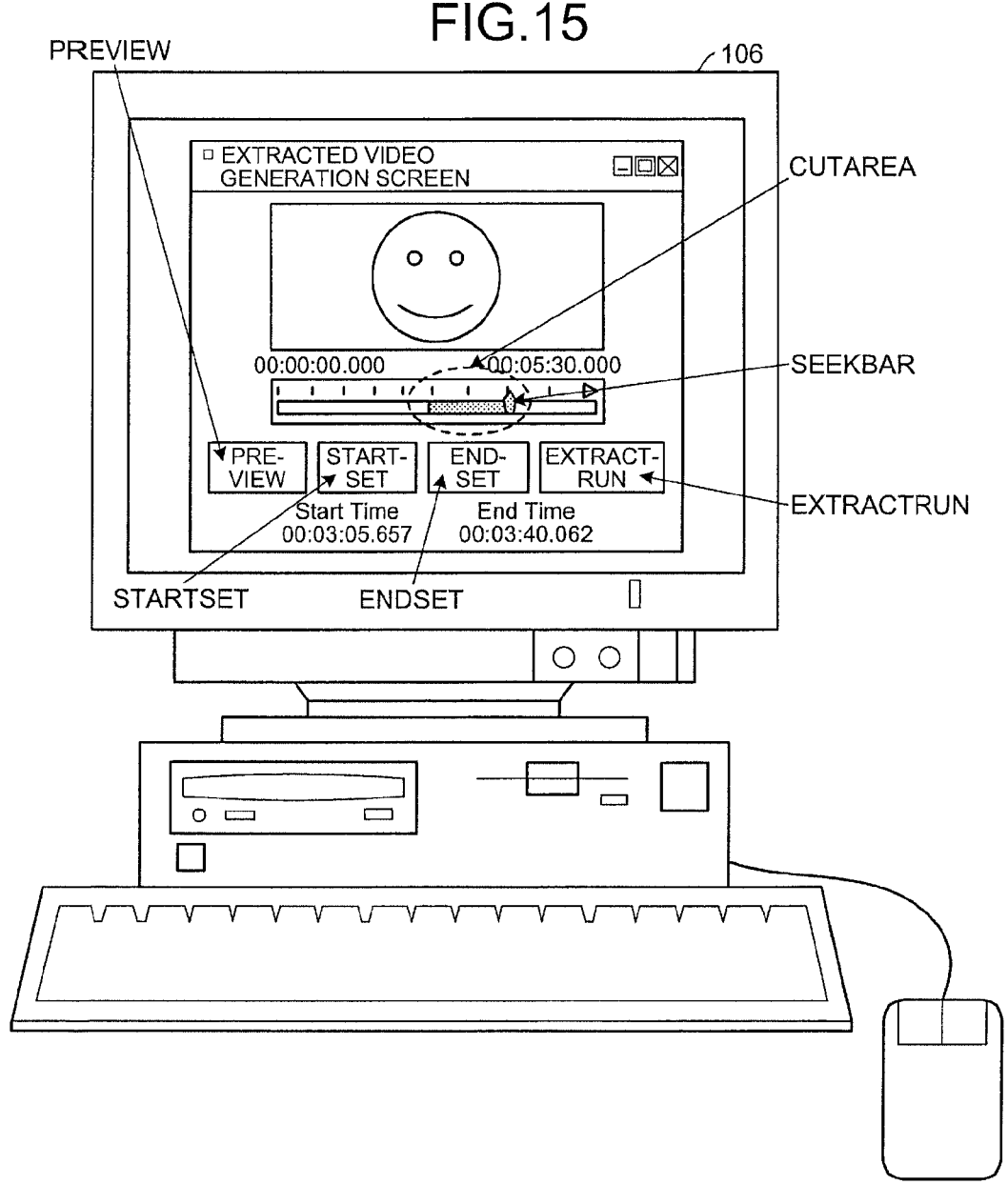
FIG. 15 depicts an extraction operation from the original video.

FIG. 15 depicts an extraction operation from the original video. As the extraction operation, a user of the extractor terminal 106 specifies a necessary portion to be extracted while playing the extracted video by a play button (PREVIEW). The user specifies a start point of extraction using a seek bar (SEEKBAR) and pushes a start button (STARTSET) at the specified point, thereby enabling the extractor terminal 106 to set the start point. Similarly, the user specifies an end point of extraction using the seek bar (SEEKBAR) and pushes an end button (ENDSET) at the specified point, thereby enabling the extractor terminal 106 to set the end point.

Thus, an extraction portion (CUTAREA) is determined, and the extractor terminal 106 generates the extracted video when an execution button (EXTRACTRUN) is pushed. In the example, it is assumed that the extractor terminal 106 extracts frames 200 to 550.

Figure 16:
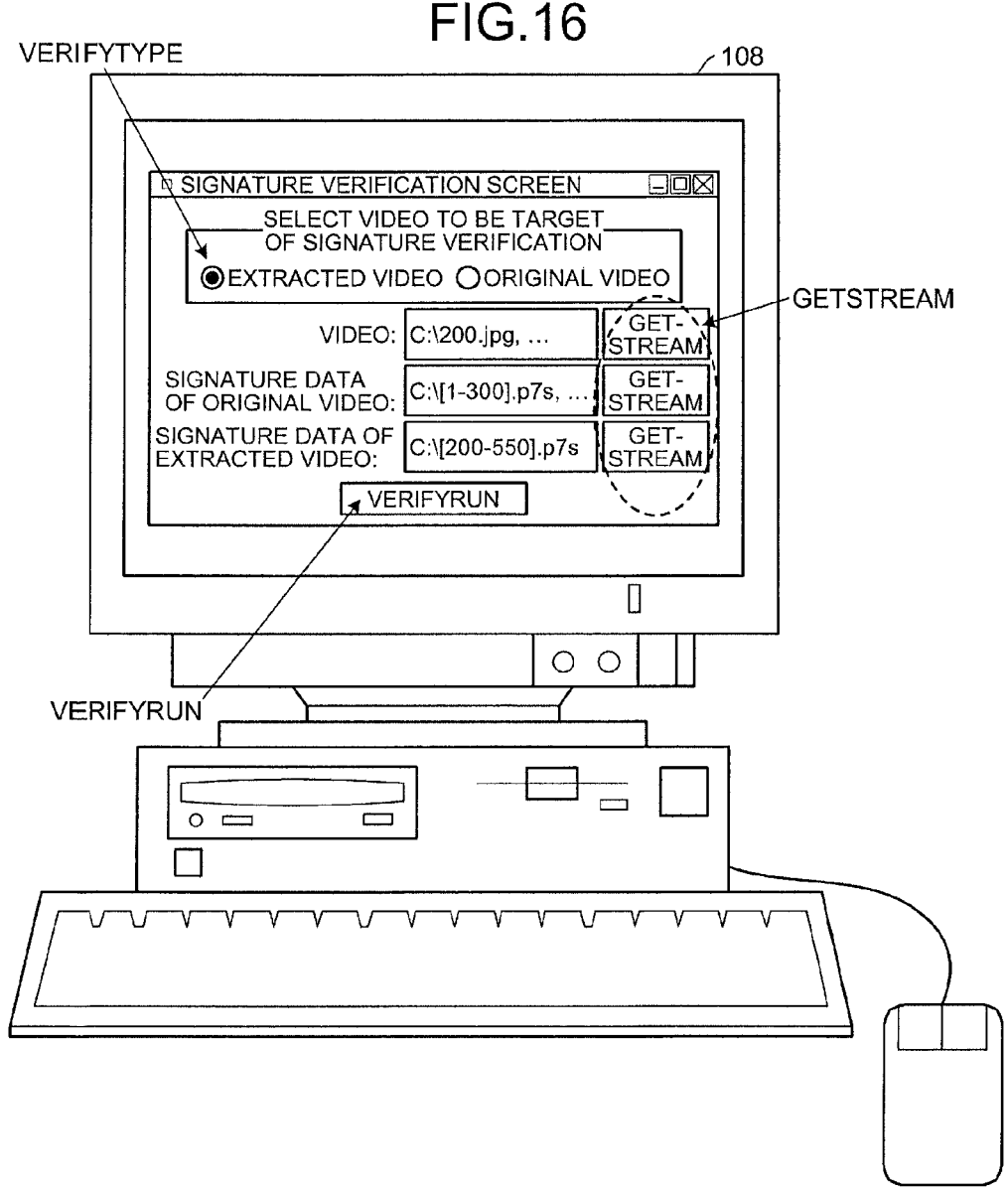
FIG. 16 depicts a selection screen for a video to be verified and data for verification.

FIG. 16 depicts a selection screen for a video to be verified and data for verification. In the example of FIG. 16, the extracted video or the original video can be selected for signature verification (VERIFYTYPE), and the verifier terminal 108 is capable of verifying both videos. When the extracted video is selected as VERIFYTYPE, for example, a verifier is enabled to select the extracted video, the signature data of the original video, and the signature data of the extracted video. The verifier can select the data through a file-selection application such as Explorer by pushing a reference button (GETSTREAM) of each field.

Specifically, the verifier can refer to and select an extracted video stored in the video management DB 501 of the signature verifying device 107 by pushing the reference button. This means selecting plural still images since the original video and the extracted video in the embodiment includes plural frames. Signature data corresponding to the selected video are also selected. The signature verification for the extracted video according to the embodiment requires the extracted video, the signature data of the original video, and the signature data of the extracted video.

Specifically, the extracted video is frames 200 to 550. The signature data of the original video are the signature data of frames 1 to 300 and the signature data of frames 301 to 600. The signature data of the extracted video is the signature data of frames 200 to 550.

When a signature verification button (VERIFYRUN) is pushed, the signature verifying device 107 executes the signature verification for the selected extracted video. In the embodiment, the verifier selects the signature data of the original video and the signature data of the extracted video. However, the verifier may select only the extracted video without being aware of the signature data (data for verification).

For example, the verifier may select the extracted video from a list of titles each of which enables the verifier to assume/identify the content of the extracted video. In this case, for example, link data have to be stored for identifying the video in the video management DB 501 of the signature verifying device 107 corresponding to the video selected from the list.

Figure 17:
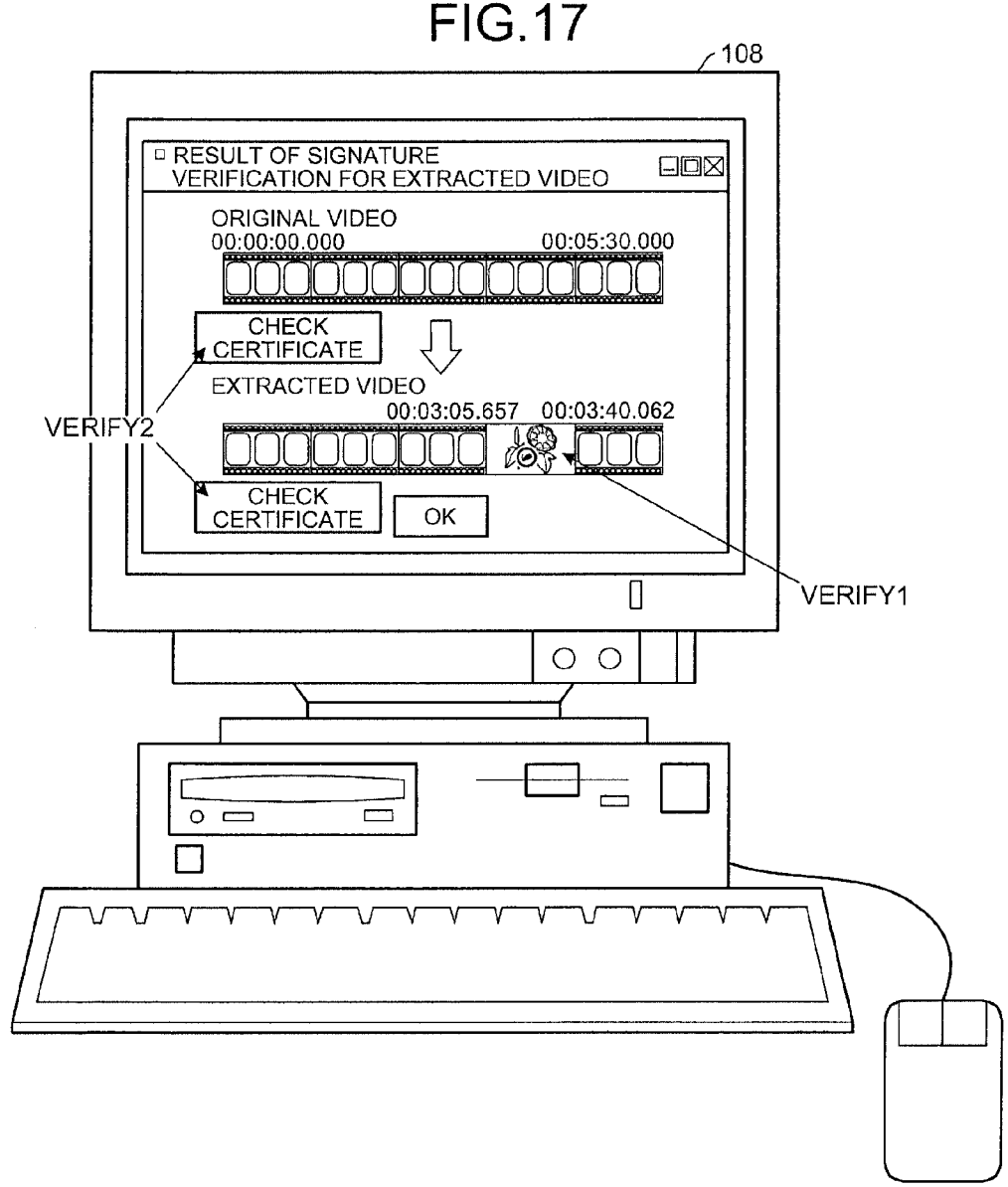
FIG. 17 depicts a result of the signature verification for the extracted video.

FIG. 17 depicts a result of the signature verification for the extracted video. By displaying the result, the verifier terminal 108 notifies the verifier that the extracted video is a part of the original video. The extraction portion indicating which part is extracted from the original video and whether the part has been changed are also displayed, thereby enabling the verifier to check the originality of the extracted video (VERIFY1). The verifier can further check which terminal has generated the original video or the extracted video by checking the digital signature of the video recorder 104 or the extractor terminal 106 (VERIFY2).

Verification with respect to the original video is also possible. For example, when the original video is selected as VERIFYTYPE in FIG. 16, the verifier using the verifier terminal 108 is able to select the original video and the signature data thereof. In this case, the signature data of the extracted video need not be selected. By pushing the reference button of each field (GETSTREAM in FIG. 16), the verifier can select the original video. Specifically, the verifier can refer to and select an original video stored in the video management DB 501 of the signature verifying device 107 by pushing the reference button.

When the signature verification button (VERIFYRUN in FIG. 16) is pushed, the signature verification for the selected original video is executed. An overview of the verification is depicted in FIG. 12 described above, and the flow of the verification will be described with reference to FIG. 23.

Using the devices described above, flows of (1) original video generation and signature generation, (2) extracted video generation and signature generation, (3) signature verification of the original video, (4) an acquisition of the extracted video, and (5) signature verification of the extracted video are described below. Flows of (6) a registration of the public key of the digital signature called by the signature generation/verification, and (7) a communication of data having digital signatures and verification by the receiving device are also described.

FIG. 18 is a flowchart of the registration of the public key of the digital signature between the sending device and the CA device 102. In the embodiment, the signature generating device 103 and the video extracting device 105 act as the sending device of the digital signature.

The sending device generates a key pair (the secret key and the public key) (step S1801), and receives a request for issuance of certificate (step S1802). The request includes data concerning the video recorder 104 or the extractor terminal 106. Thus, if there are several video recorders 104, the request may be received for each video recorder 104. If the extractor terminal 106 is used by different users, the request may be received for each user such that different public keys can be used for respective users. The sending device then sends the request and the public key to the CA device 102 (step S1803).

The CA device 102 receives the request and the public key via the communications unit 204 (step S1804). The certificate issuing unit 202 of the CA device 102 generates a public key certificate including the public key (step S1805), stores the public key certificate into the public key DB 201 (step S1806), and controls the communications unit 204 to send the public key certificate to the sending device that has sent the request via the network 101 (step S1807).

The sending device receives the public key certificate (step S1808), and stores the secret key generated at step S1801 and the public key certificate issued by the CA device 102 into a storage device of the sending device (step S1809), thereby ending the process. As the storage device, the signature generating device 103 and the video extracting device 105 use a storage device in the signature generating unit 303 and the signature generating unit 403, respectively.

FIG. 19 is a flowchart of the communication of data having digital signatures, between the sending device and the receiving device, and the verification by the receiving device in cooperation with the CA device 102. In the embodiment, the video extracting device 105 and the signature verifying device 107 act as the receiving device corresponding to the signature generating device 103 and the video extracting device 105 acting as the sending device, respectively.

The sending device encrypts the summary data (hash data) of the signature subject using the secret key stored in a storage device (step S1901) to generate the digital signature, and sends the signature subject, the digital signature, and the public key certificate also stored in the storage device to the receiving device (step S1902).

The receiving device receives the signature subject, the digital signature, and the public key certificate (step S1903), and sends the public key certificate to the CA device 102 to check the expiration date, the invalidity, etc., of the public key certificate (step S1904). In the embodiment, the CA device 102 is assumed to support functions required for the issuance and the verification of the certificate. The CA device 102 receives the public key certificate (step S1905), verifies the validity (step S1906), and sends the result of the verification to the receiving device (step S1907).

The receiving device receives the result (step S1908), and checks whether the result indicates the public key certificate is valid (step S1909). If the public key certificate is not valid (step S1909: NO), the receiving device determines that it cannot be guaranteed that no changes have occurred (step S1913), thereby ending the process. If the public key certificate is valid (step S1909: YES), the receiving device generates the summary data (hash data) of the received signature subject (step S1910), decodes the received digital signature using the public key to obtain a decoded value (step S1911), and checks whether the summary data match the decoded value (step S1912).

If the summary data and the decoded value do not match (step S1912: NO), the process proceeds to step S1913 and ends. If the summary data and the decoded value match (step S1912: YES), the receiving device determines that it can be guaranteed that no changes have occurred (step S1914) and stores the signature subject (step S1915), thereby ending the process. After step S1913, notification may be given to inform the operation terminal of the receiving device (for example, the extractor terminal 106 for the video extracting device 105 and the verifier terminal 108 for the signature verifying device 107) that the digital signature cannot be verified.

FIGS. 20A and 20B are flowcharts of the generation of the original video and of the signature. As depicted in FIG. 20A, the video recorder 104 checks whether a recording start request or a recording continue request has been received (step S2001). A recording start request is issued when the recording start button of the video recorder 104 is pushed, for example, or may be automatically issued upon powering-on. A recording continue request is issued upon reception from the signature generating device 103 that sends it at step S2011 described later.

If a recording start request or a recording continue request has been received (step S2001: YES), the video recorder 104 records a frame (step S2003), sends the frame to the signature generating device 103 (step S2004), and returns to step S2001. If neither a recording start request nor a recording continue request has been received (step S2001: NO), the video recorder 104 checks whether a recording stop request has been received (step S2002). A recording stop request is issued when the recording stop button of the video recorder 104 is pushed, for example, or may be received from the signature generating device 103.

If a recording stop request has been received (step S2002: YES), the video recorder 104 sends a recording stop instruction to the signature generating device 103 (step S2005). The recording stop instruction is a character string such as "END," and the signature generating device 103 that receives the data determines that the recording is stopped.

If the recording stop request has not been received (step S2002: NO), the video recorder 104 returns to step S2001. If the process returns to step S2001 after receiving the recording start request without receiving the recording continue request nor the recording stop request, next frame may be recorded as the recording continues (step S2001: YES, step S2003).

As depicted in FIG. 20B, the signature generating device 103 waits for a frame or a recording stop instruction from the video recorder 104 (step S2006), and upon reception of a frame or a recording stop instruction (step S2007), checks whether a recording stop instruction has been received (step S2008). If a recording stop instruction has not been received (step S2008: NO), the signature generating device 103 generates and stores a digest (frame digest) of the frame (step S2009) such as h1, h2, ..., h756 of FIG. 11 described above. The frame digest is stored in the video management DB 301 via the video management TB 302 of the signature generating device 103.

If the digest generation for "unit of block+1" frames (for example, "300+1" frames) is not completed (step S2010: NO), the signature generating device 103 sends a recording continue request to the video recorder 104 (step S2011). The video recorder 104 receives the request (step S2001), and continues to record the frames (step S2003).

If the digest generation for "unit of block+1" frames has been completed (step S2010: YES), the signature generating device 103 performs the signature generation for unsigned frame digests (step S2013), details of which will be described with reference to FIG. 21. The signature subject of the current block and the generated digital signature are stored into the video management DB 301 via the video management TB 302 of the signature generating device 103 (step S2014).

In the example of FIG. 11, the signature data of the current block is that of frames 1 to 300. The signature subject includes "StartInfo," frame digests h1 to h300, and frame digest h301 denoted by "ContinueInfo-1-1." The digital signature is the digital signature 1104 of the video recorder 104.

The signature generating device 103 then checks whether a recording stop instruction has been received (step S2015). If a recording stop instruction has not been received (step S2015: NO; this is always the case when step S2010: YES), the process proceeds to step S2011 and the signature generating device 103 sends the recording continue request to the video recorder 104 (step S2011). Processes after the recording stop instruction has been received (step S2015: YES) will be described later. The signature generating device 103 then waits for the frame (step S2006).

On the other hand, if a recording stop instruction has been received at step 2008 (step S2008: YES), the signature generating device 103 checks whether an unsigned frame digest(s) exists (step S2012). If so (step S2012: YES), the signature generating device 103 performs signature generation for the unsigned frame digest(s) (step S2013), and stores the signature subject and the digital signature into the video management DB 301 (step S2014).

In this case (step S2008: YES, step S2012: YES), the signature data of the current block is that of frames 601 to 756 depicted in FIG. 11 after reception of which, the recording stop instruction is received. The signature subject includes frame digest h600 denoted by "ContinueInfo-2-2," frame digests h601 to h756, and a character string such as "NULL" denoted by "EndInfo." The digital signature is the digital signature 1106 of the video recorder 104.

The signature generating device 103 then checks whether a recording stop instruction has been received (step S2015). If a recording stop instruction has been received (step S2015: YES; this is always the case when step S2008: YES), or if no unsigned frame digest exists (step S2012: NO), the signature generating device 103 sends the original video, the signature subject, and the digital signature to the video extracting device 105 (step S2016). The signature generating device 103 then waits for the frame (step S2006).

The original video is frames 1 to 756, and the signature subject and the digital signature are those depicted in FIG. 11. The first block corresponds to frames 1 to 300. The signature subject includes the start ID such as "START" denoted by "StartInfo" in FIG. 11, frame digests h1 to h300, and frame digest h301 denoted by "ContinueInfo-1-1." The digital signature is the digital signature 1104 of the video recorder 104 appended to the signature subject.

The second block corresponds to frames 301 to 600. The signature subject includes frame digest h300 denoted by "ContinueInfo-1-2," frame digests h301 to h600, and frame digest h601 denoted by "ContinueInfo-2-1." The digital signature is the digital signature 1105 of the video recorder 104 appended to the signature subject.

The third block corresponds to frames 601 to 756. The signature subject includes frame digest h600 denoted by "ContinueInfo-2-2," frame digests h601 to h756, and the end ID such as "NULL" denoted by "EndInfo." The digital signature is the digital signature 1106 of the video recorder 104 appended to the signature subject.

The video extracting device 105 waits for the original video, the signature subject, and the digital signature (step S2017). Upon reception thereof (step S2018), the video extracting device 105 stores the received data into the video management DB 401 via the video management TB 402 (step S2019), thereby ending the original video generation and the signature generation.

In the embodiment, the signature generating device 103 and the video extracting device 105 (i.e., functions of signature generation and functions of extraction) are separately provided. However, the signature generating device 103 may perform the signature generation, storing/management, and the extraction. In this case, the video extracting device 105 may omitted.

FIG. 21 is a flowchart of the signature generation with respect to frame digests, in which the signature subject and the digital signature are generated with respect to a target block. This process inherits the portion of unsigned frame digest(s) as an argument.

The signature generating device 103 checks whether a recording stop instruction has been received (step S2101). If a recording stop instruction has not been received (step S2101: NO), the signature generating device 103 excluding the last frame digest, puts the input portion of frame digest(s) on a list of portions guaranteed by digital signature (step S2102). If a recording stop instruction has been received (step S2101: YES), the signature generating device 103 puts the input portion of frame digest(s) on the list (step S2103).

The list of portions guaranteed by digital signature is a variable that indicates up to which frame the target block extends. The last frame digest is excluded because if the recording stop instruction has not been received, the last frame digest is located in the next block and used to guarantee the continuity of the target block and the next block.

The signature generating device 103 copies the list to the signature subject (step S2104), and checks whether the copied signature subject is located at the beginning of the original video (step S2105). If the copied signature subject is not at the beginning (step S2105: NO), the signature generating device 103 appends to the beginning of the signature subject as a digest for continuity verification, the frame digest located at the end of the frame digests, to which the digital signature has been appended (step S2106). In the example of FIG. 11, "h300" and "h600" denoted by "ContinueInfo-1-2" and "ContinueInfo-2-2" are digests for continuity verification for the second block and the third block, respectively.

If the copied signature subject is located at the beginning of the original video (step S2105: YES), the signature generating device 103 appends the start ID to the beginning of the signature subject (step S2107). In the example of FIG. 11, the start ID is a character string such as "START" set at the beginning of the first block and denoted by "StartInfo."

After the head portion is determined, the end portion is also determined in a similar manner. The signature generating device 103 checks whether a recording stop instruction has been received (step S2108). If a recording stop instruction has not been received (step S2108: NO), the signature generating device 103 appends to the end of the signature subject as a digest for continuity verification, the frame digest located at the end of input frame digests (step S2109). In the example of FIG. 11, "h301" and "h601" denoted by "ContinueInfo-1-1" and "ContinueInfo-2-1" are digests for continuity verification for the first block and the second block, respectively.

If a recording stop instruction has been received (step S2108: YES), the signature generating device 103 appends the end ID to the end of the signature subject (step S2110). In the example of FIG. 11, the end ID is a character string such as "NULL" set at the end of the third block and denoted by "EndInfo."

After the signature subject is set, the signature generating device 103 generates the digital signature of the video recorder 104 with respect to the signature subject (step S2111), and sets the frame digests included in the list of portions guaranteed by digital signature as signed frame digests (step S2112). Thus, the signature subject can include data enabling the integrity concerning the continuity of the target block and the preceding/next block(s) to be guaranteed at the time of verification.

Figure 22A:
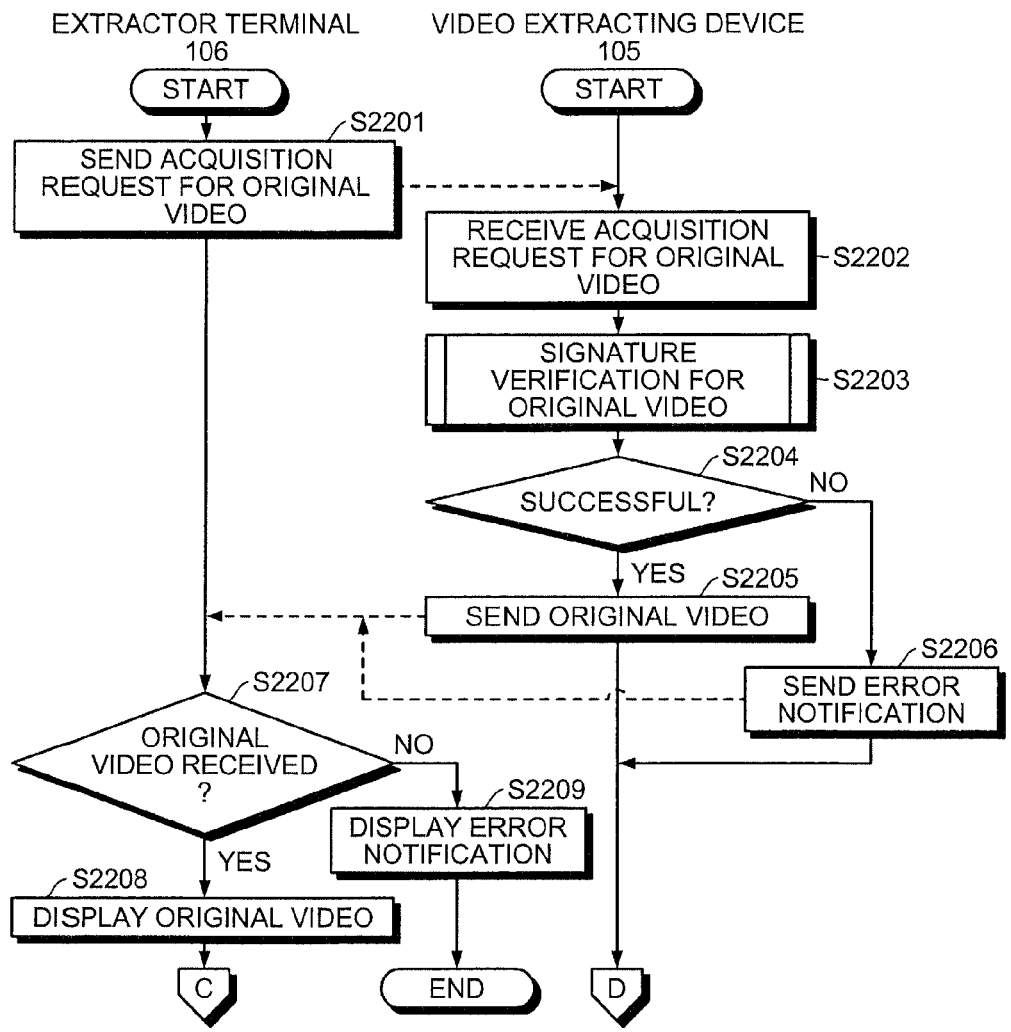

FIGS. 22A and 22B are flowcharts of the generation of the extracted video and of the signature. The original video is required to generate the extracted video. Thus, first the original video is obtained according to FIG. 22A, and then the extracted video is generated according to FIG. 22B.

As depicted in FIG. 22A, the extractor terminal 106 sends to the video extracting device 105, an acquisition request for the original video from which video is to be extracted (step S2201), and waits for a response from the video extracting device 105.

The video extracting device 105 receives the request (step S2202), and obtains the original video and the signature data stored in the video management DB 401 via the video management TB 402. The video extracting device 105 performs the signature verification for the original video by the signature verifying unit 404 (step S2203), details of which will be described with reference to FIG. 23, to check before the extraction, whether the original video has been falsified.

The video extracting device 105 then checks whether the verification of the original video is successful (step S2204). If verification is successful (step S2204: YES), the video extracting device 105 sends the original video to the extractor terminal 106 (step S2205), and if not successful (step S2204: NO), sends an error notification (step S2206).

The extractor terminal 106 checks what has been received from the video extracting device 105 (step S2207), and if the original video has been received (step S2207: YES), the extractor terminal 106 displays the original video (step S2208) and generates the extracted video. If the original video has not been received, in other words, an error notification has been received (step S2207: NO), the extractor terminal 106 displays the error notification (step S2209), thereby ending the process.

As depicted in FIG. 22B, the extractor terminal 106 generates the extracted video (step S2210). An overview of the generation is depicted in FIG. 15 described above. In the embodiment, it is assumed that frames 200 to 550 are extracted. The extractor terminal 106 then sends the extracted video to the video extracting device 105 (step S2211).

The video extracting device 105 receives the extracted video (step S2212), and the signature generating unit 403 generates signature data with respect to the extracted video. An overview of the generation is depicted in FIG. 13 described above. The video extracting device 105 obtains the head frame of the extracted video (step S2213) such as frame 200 of FIG. 13, and generates and stores the frame digest of the frame (step S2214). The video extracting device 105 checks whether the obtained frame is the end frame (step S2215), and if the frame is not the end frame (step S2215: NO), obtains the next frame (step S2216) and generates and stores the frame digest (step S2214).

If the end frame has been reached (step S2215: YES), the video extracting device 105 generates the digital signature 1302 of the extractor terminal 106 depicted in FIG. 13 with respect to frame digests h200, h201, . . . , h550 (step S2217).

After the generation of the signature data including the signature subject and the digital signature with respect to the extracted video, the video extracting device 105 stores the extracted video, the signature subject, and the digital signature as a combination into the video management DB 401 via the video management TB 402 (step S2218), and sends the extracted video, the signature subjects and the digital signatures of the original video, and the signature subject and the digital signature of the extracted video to the signature verifying device 107 via the communications unit 405 (step S2219). The signature verifying device 107 receives the data via the communications unit 504 (step S2220), and stores the data into the video management DB 501 via the video management TB 502 (step S2221).

FIG. 23 is a flowchart of the signature verification for the original video, an overview of which is depicted in FIG. 12 described above. The video extracting device 105 verifies the digital signature for each block, confirming that none of the signature data have been falsified since the time of generation (step S2301). In the example of FIG. 12, the digital signatures to be checked are the digital signatures 1201 to 1203 of the video recorder 104.

If the verification is successful (step S2301: YES), the video extracting device 105 checks whether a head signature and an end signature are appended to the signature subject (step S2302). The head signature is located at the beginning of the signature subject of the head block, and in FIG. 12, the head signature 1204 is the start ID such as "START." The end signature is located at the end of the signature subject of the end block, and in FIG. 12, the end signature 1205 is the end ID such as "NULL."

If the head signature and the end signature are appended (step S2302: YES), the video extracting device 105 obtains the head frame of the original video (step S2303), and generates the frame digest of the frame (step S2304). This corresponds to the digest generation 1206 of FIG. 12, and h1, h2, . . . , h756 are generated.

The video extracting device 105 then checks whether the generated frame digest matches the frame digest recorded in the signature subject (step S2305). This corresponds to the comparisons 1207 to 1209 of FIG. 12.

If the digests match (step S2305: YES), the video extracting device 105 checks whether the generated frame digest is used as the digest for continuity verification (step S2306). In the example of FIG. 12, frame digests h300, h301, h600, and h601 are used as digests for continuity verification. If the frame digest is not used (step S2306: NO), the process proceeds to step S2308.

If the frame digest is used (step S2306: YES), the video extracting device 105 checks whether the generated frame digest matches the digest for continuity verification (step S2307). This corresponds to the continuity checks 1210 and 1211 of FIG. 12.

If the digests match (step S2307: YES), or if the generated frame digest is not used as the digest for continuity verification (step S2306: NO), the verification for the obtained frame is completed and thus, the video extracting device 105 checks whether the frame is the end frame (step S2308). If the frame is not the end frame (step S2308: NO), the video extracting device 105 obtains the next frame (step S2310) and generates the frame digest with respect to the next frame (step S2304), thereby continuing the verification. If the frame is the end frame (step S2308: YES), the signature verification for the original video is successful (step S2309), and the video extracting device 105 sends the original video to the extractor terminal 106.

On the other hand, the verification fails if step S2301: NO, step S2302: NO, step S2305: NO, or step S2307: NO, and the video extracting device 105 notifies the extractor terminal 106 of the failure (step S2311).

FIG. 24 is a flowchart of the acquisition of the extracted video. The verifier terminal 108 sends an acquisition instruction for the extracted video to the signature verifying device 107 (step S2401). Acquisition of the extracted video is described with reference to FIG. 16. The verifier terminal 108 then waits for a response from the signature verifying device 107.

The signature verifying device 107 receives the instruction (step S2402), and obtains the extracted video, the signature subjects and the digital signatures of the original video, and the signature subject and the digital signature of the extracted video stored in the video management DB 501 via the video management TB 502 (step S2403). The signature verifying device 107 performs the signature verification for the extracted video by the signature verifying unit 503 (step S2404), the details of which will be described with reference to FIG. 25.

The signature verifying device 107 then checks whether the verification of the extracted video is successful (step S2405). If verification is successful (step S2405: YES), the signature verifying device 107 sends the result of the verification to the verifier terminal 108 (step S2406), while if not successful (step S2405: NO), sends an error notification (step S2407).

The verifier terminal 108 checks what has been received from the signature verifying device 107 (step S2408), and if the result has been received (step S2408: YES), the verifier terminal 108 displays the result (step S2409). If the result has not been received, in other words, error notification has been received (step S2408: NO), the verifier terminal 108 displays the error notification (step S2410).

Figure 25:
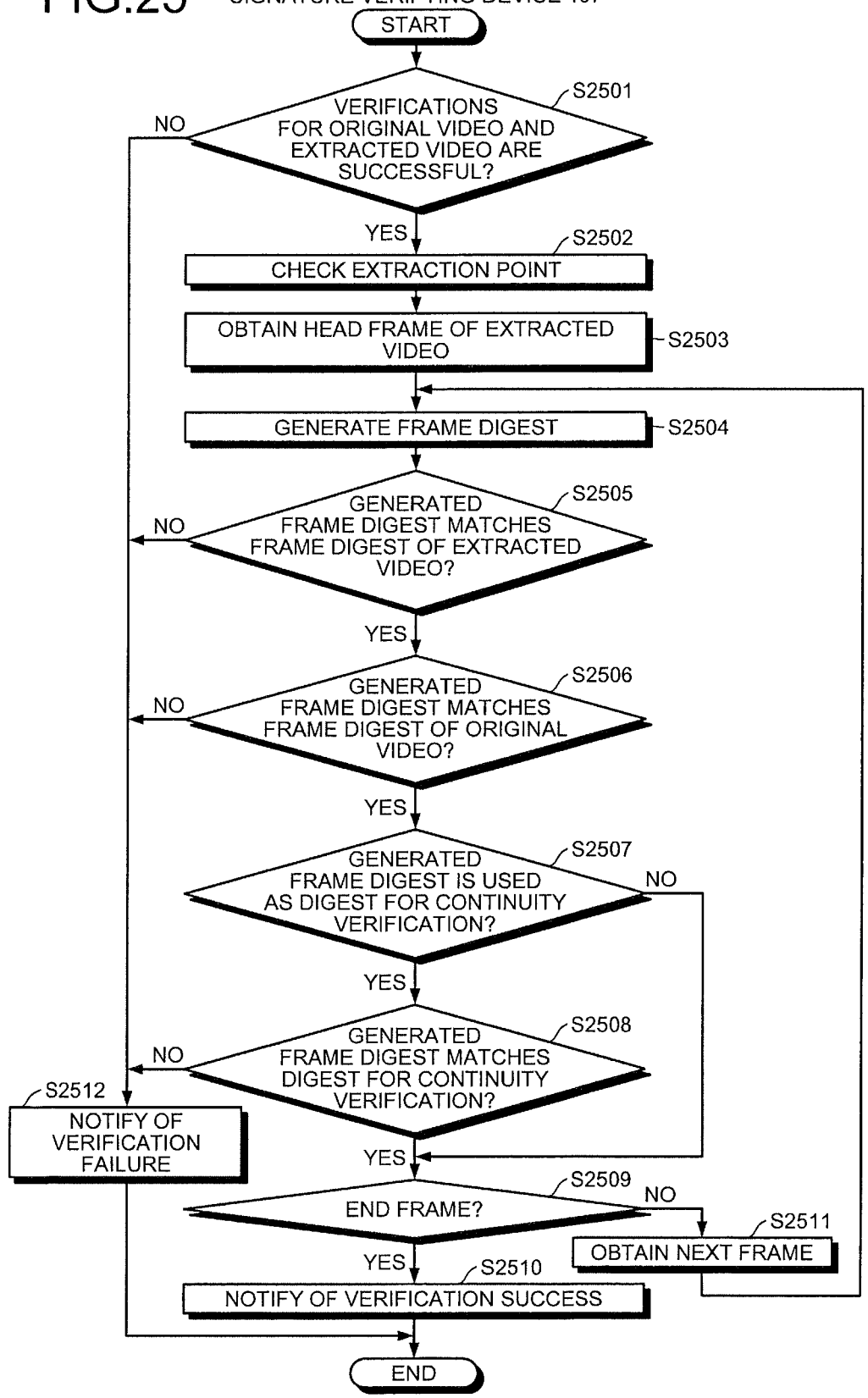
FIG. 25 is a flowchart of the signature verification for the extracted video.

FIG. 25 is a flowchart of the signature verification for the extracted video, an overview of which is depicted in FIG. 14 described above. The signature verifying device 107 performs the verification of the digital signature for each block of the original video and the verification of the digital signature of the extracted video, confirming that none of the signature data have been falsified since the time of generation (step S2501). In the example of FIG. 14, the digital signatures to be checked are the digital signatures 1401 and 1402 of the video recorder 104 and the digital signature 1403 of the extractor terminal 106.

If the verification is successful (step S2501: YES), the signature verifying device 107 checks the extraction point based on the head signature and the end signature included in the signature subject of the original video (step S2502). The head signature is located at the beginning of the signature subject of the head block, and in FIG. 14, the head signature 1404 is the start ID such as "START." The end signature is located at the end of the signature subject of the end block, and in FIG. 14, the end signature 1405 is the frame digest h601 of frame 601. Since the end signature 1405 is not the end ID such as "NULL," it can be discerned that there are subsequent digital signatures.

The signature verifying device 107 then obtains the head frame of the extracted video (step S2503), and generates the frame digest of the frame (step S2504). This corresponds to the digest generation 1406 of FIG. 14, and h200, h201, . . . , h550 are generated.

The signature verifying device 107 then checks whether the generated frame digest matches the frame digest recorded in the signature subject of the extracted video (step S2505). This corresponds to the comparison 1407 of FIG. 14.

If the digests match (step S2505: YES), the signature verifying device 107 checks whether the generated frame digest matches the frame digest recorded in the signature subject of the original video (step S2506). This corresponds to the comparisons 1408 and 1409 of FIG. 14.

If the digests match (step S2506: YES), the signature verifying device 107 checks whether the generated frame digest is used as the digest for continuity verification (step S2507). In FIG. 14, frame digests h300 and h301 are used as the digest for continuity verification. If the digest is not used (step S2507: NO), the process proceeds to step S2509.

If the digest is used (step S2507: YES), the signature verifying device 107 checks whether the generated frame digest matches the digest for continuity verification (step S2508). This corresponds to the continuity check 1410 of FIG. 14.

If the digests match (step S2508: YES), or if the generated frame digest is not used as the digest for continuity verification (step S2507: NO), the verification for the obtained frame is completed and thus, the signature verifying device 107 checks whether the frame is the end frame (step S2509). If the frame is not the end frame (step S2509: NO), the signature verifying device 107 obtains the next frame (step S2511) and generates the frame digest with respect to the next frame (step S2504), thereby continuing the verification. If the frame is the end frame (step S2509: YES), the signature verification for the extracted video is successful, and the signature verifying device 107 sends the result thereof to the verifier terminal 108 (step S2510).

On the other hand, the verification fails if step S2501: NO, step S2505: NO, step S2506: NO, or step S2508: NO, and the signature verifying device 107 notifies the verifier terminal 108 of the failure (step S2512).

As described above, the signature generating device 103 according to the embodiment divides the sequence of data into blocks, and appends the digital signature to the target block using a message digest(s) included in at least one among the preceding block and the next block. The continuity of the blocks can be guaranteed by the digital signature.

A message digest(s) in the next block may be used, in which case, the continuity and order of the target block and the next block can be guaranteed. Further, it can be guaranteed that the target block is not located at the end of the data, in other words, other data exist after the target block.

Message digest(s) from both the preceding block and the next block may be used, in which case, the continuity and order of the preceding block, the target block, and the next block can be guaranteed. Further, it can be guaranteed that the target block is not located at the beginning/end of the data, in other words, other data exists before and after the target block.

The message digest of the next block may be the message digest located at the beginning of the next block. In this case, the digital signature can be quickly generated.

A message digest(s) in the preceding block may be used, in which case, the continuity and order of the preceding block and the target block can be guaranteed. Further, it can be guaranteed that the target block is not located at the beginning of the data, in other words, other data exists before the target block.

If the target block is the head block, the digital signature may be appended to data including the identifier indicating the head block. In this case, it can be guaranteed that the target block is located at the beginning of the data and no other false block has been connected before the target block by falsification.

If the target block is the end block, the digital signature may be appended to data including the identifier indicating the end block. In this case, it can be guaranteed that the target block is located at the end of the data and no other false block has been connected after the target block by falsification.

The sequence of data may be frames extracted from video data at a given time interval. Since the message digests can be compared for each frame, the embodiment is applicable to any video format that manages data in units of frame.

The signature verifying device 107 according to the embodiment receives the digital signature appended to data including the message digest(s) included in the preceding/next block(s). The continuity of the blocks can be guaranteed by verifying the digital signature.

If a message digest(s) in the next block is used, the continuity and order of the target block and the next block can be guaranteed, and replacement or intermediate extraction of block(s) can be prevented.

If message digests from both the preceding and the next block are used, the continuity and order of the preceding block, the target block, and the next block can be guaranteed, and replacement or intermediate extraction of block(s) can be prevented.

If a message digest(s) in the preceding block is used, the continuity and order of the preceding block and the target block can be guaranteed, and replacement or intermediate extraction of block(s) can be prevented.

If the target block is the head block, the digital signature appended to data including the identifier indicating the head block may be received. In this case, it can be verified that the target block is the head block, and a false block is prevented from being connected before the target block.

If the target block is the end block, the digital signature appended to data including the identifier indicating the end block may be received. In this case, it can be verified that the target block is the end block, and a false block is prevented from being connected after the target block.

To reduce the amount of the signature data, the hash data may be managed by a binary tree disclosed in, for example, Japanese Laid-Open Patent Publication No. 2008-178048.

According to the embodiment, it can be proven to a third party that video recorded in real-time and over a long period of time has not been falsified and further that the video has been recorded continuously over time without any intermediate extraction, replacement, etc. Further, even if a part the original video is extracted for the protection of privacy, for example, the extraction point can be detected and the originality of the extracted video can be verified. Furthermore, even if the extractor or other third party has made a change, addition, etc., to the extracted video, the extractor can be identified from the digital signature applied to the signature data and thus, be tracked easily.

The data used in the embodiment are video data, however, may be audio data continuously input from, for example, a security microphone or a sequence of text data such as an access log of a web server operating 24 hours. The embodiment is applicable to such data by generating the frame digest by the signature generating device 103 with respect to a one-day log generated by the web server, and generating the digital signature with respect to a one-month log that constitute the signature subject.

The signature generating method and the signature verifying method described in the present embodiment may be implemented by executing a prepared program on a computer such as a personal computer and a workstation. The program is stored on a computer-readable recording medium such as a hard disk, a flexible disk, a CD-ROM, an MO, and a DVD, read out from the recording medium, and executed by the computer. The computer-readable recording medium or storage device mentioned herein does not include, for example, a transitory propagation signal, or the like. The program may be distributed through a network such as the Internet using a transmission medium. An example of a transmission medium includes a carrier-wave signal.

The embodiments can verify a digital signature, providing guarantee, to a third party, that no intermediate removal, replacement, etc., has occurred.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A signature generating device comprising:
a processor configured to execute:
receiving data sequentially;
sequentially generating summary data of the data upon reception of the data;
obtaining a sequence of the summary data as a block when a number associated with the summary data generated reaches a given number;
setting, as a signature subject, a current block constituted by the sequence of the summary data and the summary data selected from at least one block contiguous to the current block;
generating a digital signature with respect to the signature subject; and
sending the generated digital signature, the signature subject associated with the digital signature, and the data summarized for the current block,
wherein the summary data is a digest of a frame obtained by substituting the frame received at the receiving into a hash function as an argument.

2. The signature generating device according to claim 1, wherein the setting sets the current block and the summary data selected from a next block as the signature subject.

3. The signature generating device according to claim 1, wherein the setting sets the current block, the summary data selected from a preceding block, and the summary data selected from a next block as the signature subject.

4. The signature generating device according to claim 2, wherein the summary data selected from the next block is the summary data located at a beginning of the next block.

5. The signature generating device according to claim 1, wherein the setting sets a current block and the summary data selected from a preceding block as the signature subject.

6. The signature generating device according to claim 2, wherein when the current block is a head block, the setting sets, as the signature subject, the current block, the summary data selected from the next block, and an identifier indicating that the current block is the head block.

7. The signature generating device according to claim 5, wherein when the current block is an end block, the setting sets, as the signature subject, the current block, the summary data selected from the preceding block, and an identifier indicating that the current block is the end block.

8. The signature generating device according to claim 1, wherein the receiving receives, as the data, a frame extracted from video data at a given time interval.

9. A signature generating method executed by a computer including a processor, the signature generating method comprising:
   receiving data sequentially;
   generating sequentially summary data of the data upon reception of the data;
   obtaining a sequence of the summary data as a block when a number associated with the summary data generated reaches a given number;
   setting, as a signature subject, a current block constituted by the sequence of the summary data and the summary data selected from at least one block contiguous to the current block;
   generating, using the processor, a digital signature with respect to the signature subject; and sending the generated digital signature, the signature subject associated with the digital signature, and the data summarized of the current block,
   wherein the summary data is a digest of a frame obtained by substituting the frame received at the receiving into a hash function as an argument.

10. A non-transitory computer-readable recording medium storing therein a signature generating program causing a computer to execute a process comprising:
    receiving data sequentially;
    generating sequentially summary data of the data upon reception of the data;
    obtaining a sequence of the summary data as a block when a number associated with the summary data generated reaches a given number;
    setting, as a signature subject, a current block constituted by the sequence of the summary data, and the summary data selected from at least one block contiguous to the current block;
    generating a digital signature concerning data summarized for the current block; and sending the generated digital signature, the signature subject associated with the digital signature, and the data summarized for the current block,
    wherein the summary data is a digest of a frame obtained by substituting the frame received at the receiving into a hash function as an argument.

11. A signature verifying device comprising:
    a receiving unit configured to receive data sequentially, wherein summary data of the data is handled in blocks respectively constituted by a sequence of the summary data of a given number;
    a signature subject constituted by a current block subject to verification, and summary data selected from at least one block contiguous to the current block;
    a digital signature generated with respect to the signature subject;
    a summary data generating unit configured to respectively generate the summary data of the data received by the receiving unit;
    a signature subject verifying unit configured to verify the integrity of the signature subject, based on the digital signature;
    a data verifying unit configured to verify the integrity of the data, based on the signature subject verified by the signature subject verifying unit and the generated summary data;
    a continuity verifying unit configured to verify the continuity of the current block and the block contiguous to the current block, based on the generated summary data selected from the block contiguous to the current block and the summary data constituting the signature subject; and a digital signature verifying unit configured to verify the integrity of the data, based on verification results obtained by the signature subject verifying unit and the continuity verifying unit,
    wherein the summary data is a digest of a frame obtained by substituting the frame received at the receiving into a hash function as an argument.

12. The signature verifying device according to claim 11, wherein
    when the summary data constituting the signature subject is selected from a next block of the current block, the receiving unit receives the data, the signature subject constituted by the current block and the summary data selected from the next block, and the digital signature generated with respect to the signature subject, and
    the continuity verifying unit verifies the continuity and order of the current block and the next block, based on the generated summary data selected from the next block and the summary data constituting the signature subject.

13. The signature verifying device according to claim 11, wherein
    when the summary data constituting the signature subject is selected from a preceding block and a next block of the current block, the receiving unit receives the data, the signature subject constituted by the current block, the summary data selected from the preceding block, and the summary data selected from the next block, and the digital signature generated with respect to the signature subject, and
    the continuity verifying unit verifies the continuity and order of the preceding block and the current block, based on the generated summary data selected from the preceding block and the summary data constituting the signature subject and selected from the preceding block, and the continuity and order of the current block and the next block, based on the generated summary data selected from the next block and the summary data constituting the signature subject and selected from the next block.

14. The signature verifying device according to claim 11, wherein
    when the summary data constituting the signature subject is selected from a preceding block of the current block, the receiving unit receives the data, the signature subject constituted by the current block and the summary data selected from the preceding block, and the digital signature generated with respect to the signature subject and concerns data summarized for the current block, and
    the continuity verifying unit verifies the continuity and order of the preceding block and the current block, based on the generated summary data selected from the preceding block and the summary data constituting the signature subject.

15. The signature verifying device according to claim 12, wherein
the receiving unit receives the data,
the signature subject constituted by the current block, the summary data selected from the next block, and an identifier indicating the start of the sequence of the data, and
the digital signature generated with respect to the signature subject, and
the continuity verifying unit verifies the continuity and order of the current block and the next block, based on the generated summary data selected from the next block and the summary data constituting the signature subject, and
the current block to be a head block, based on the identifier.

16. The signature verifying device according to claim 14, wherein
the receiving unit receives the data,
the signature subject constituted by the current block, the summary data selected from the preceding block, and an identifier indicating the end of the sequence of the data, and the digital signature generated with respect to the signature subject, and
the continuity verifying unit verifies the continuity and order of the preceding block and the current block, based on the generated summary data selected from the preceding block and the summary data constituting the signature subject, and
the current block to be an end block, based on the identifier.

17. A signature verifying method executed by a computer including a receiving unit, a summary data generating unit, a signature subject verifying unit, a data verifying unit, a continuity verifying unit, and a digital signature verifying unit, the signature verifying method comprising:
receiving data by the receiving unit sequentially, wherein summary data of the data is handled in blocks respectively constituted by a sequence of the summary data of a given number, a signature subject constituted by a current block subject to verification, and summary data selected from at least one block contiguous to the current block, and a digital signature generated with respect to the signature subject;
generating respectively by the summary data generating unit, the summary data of the data received at the receiving;
verifying by the signature subject verifying unit, integrity of the signature subject, based on the digital signature;
verifying by the data verifying unit, the integrity of the data, based on the signature subject verified at the verifying the signature subject and the generated summary data;
verifying by the continuity verifying unit, continuity of the current block and the block contiguous to the current block, based on the generated summary data selected from the block contiguous to the current block and the summary data constituting the signature subject; and
verifying, by the digital signature verifying unit, integrity of an order of the data, based on verification results obtained at the verifying the signature subject and at the verifying the continuity.

18. A non-transitory computer-readable recording medium storing therein a signature verifying program causing a computer to execute a process comprising:
receiving data sequentially, wherein summary data of the data is handled in blocks respectively constituted by a sequence of the summary data of a given number, a signature subject constituted by a current block subject to verification, and summary data selected from at least one block contiguous to the current block, and a digital signature generated with respect to the signature subject;
generating respectively the summary data of the data received at the receiving;
verifying integrity of the signature subject, based on the digital signature;
verifying integrity of the data, based on the signature subject verified at the verifying the signature subject and the generated summary data;
verifying continuity of the current block and the block contiguous to the current block, based on the generated summary data selected from the block contiguous to the current block and the summary data constituting the signature subject; and
verifying integrity of an order of the data, based on verification results obtained at the verifying the signature subject and the verifying the continuity.

* * * * *